US011587484B2

(12) United States Patent
Sadornil et al.

(10) Patent No.: US 11,587,484 B2
(45) Date of Patent: Feb. 21, 2023

(54) METHOD FOR CONTROLLING A DISPLAY

(71) Applicant: Amer Sports Digital Services Oy, Vantaa (FI)

(72) Inventors: Ramon Sadornil, Vantaa (FI); Erik Lindman, Vantaa (FI); Timo Eriksson, Vantaa (FI); Jari Akkila, Vantaa (FI); Tuomas Hapola, Vantaa (FI); Mikko Martikka, Vantaa (FI)

(73) Assignee: Suunto Oy, Vantaa (FI)

( * ) Notice: Subject to any disclaimer, the term of this patent is extended or adjusted under 35 U.S.C. 154(b) by 0 days.

(21) Appl. No.: 16/731,104

(22) Filed: Dec. 31, 2019

(65) Prior Publication Data

US 2020/0135076 A1    Apr. 30, 2020

Related U.S. Application Data

(63) Continuation-in-part of application No. 16/228,981, filed on Dec. 21, 2018, and a continuation-in-part of
(Continued)

(30) Foreign Application Priority Data

Dec. 21, 2015   (FI) ...................................... 20155989
Dec. 21, 2015   (GB) ...................................... 1522525
(Continued)

(51) Int. Cl.
   *G06F 3/02*       (2006.01)
   *G09G 3/04*       (2006.01)
   *G06F 1/16*       (2006.01)

(52) U.S. Cl.
   CPC ............... *G09G 3/04* (2013.01); *G06F 1/163* (2013.01); *G06F 3/02* (2013.01); *G09G 2330/021* (2013.01)

(58) Field of Classification Search
   CPC ............... G09G 3/04; G09G 2330/021; G09G 2354/00; G09G 2360/144; G06F 3/02;
   (Continued)

(56) References Cited

U.S. PATENT DOCUMENTS 5,457,284 A   10/1995  Ferguson
5,503,145 A    4/1996  Clough
(Continued)

FOREIGN PATENT DOCUMENTS

AU    2007216704 A1    4/2008
CN       1877340 A1   12/2006
(Continued)

OTHER PUBLICATIONS

ARM big. LITTLE. Wikipedia, The free encyclopedia, Oct. 11, 2018, Retrieved on May 28, 2020 from: <https://en.wikipedia.org/w/index.php?title=ARM_bit.LITTLE&oldid=863559211> foreword on p. 1, section "Run-state migration" on pp. 1-2.
(Continued)

*Primary Examiner* — Eyob Hagos
(74) *Attorney, Agent, or Firm* — Laine IP Oy

(57) ABSTRACT

There is provided an apparatus comprising at least one processor; and at least one memory including computer program code, the at least one memory and the computer program code configured to, with the at least one processor, cause the apparatus at least to perform: receiving an activity type of a user; receiving sensor data; determining at least one measurement value based on the sensor data; detecting at least one first activity type specific change in the at least one measurement value; and activating a display in response to detecting the at least one first activity type specific change in the at least one measurement value.

13 Claims, 9 Drawing Sheets

Related U.S. Application Data application No. 15/784,234, filed on Oct. 16, 2017, now Pat. No. 11,145,272, said application No. 16/228,981 is a continuation-in-part of application No. 15/386,062, filed on Dec. 21, 2016, now Pat. No. 10,433,768, and a continuation-in-part of application No. 15/386,074, filed on Dec. 21, 2016, now Pat. No. 10,327,673, and a continuation-in-part of application No. 15/386,050, filed on Dec. 21, 2016, now Pat. No. 10,856,776, and a continuation-in-part of application No. 15/382,763, filed on Dec. 19, 2016.

(30) Foreign Application Priority Data

| Sep. 20, 2016 | (FI) | 20165707 |
|---|---|---|
| Sep. 20, 2016 | (FI) | 20165709 |
| Sep. 20, 2016 | (FI) | 20165710 |
| Oct. 17, 2016 | (FI) | 20165790 |
| Oct. 17, 2016 | (GB) | 1617575 |

(58) Field of Classification Search
CPC ...... G06F 1/163; G06F 1/1684; G06F 1/1694; G06F 1/3215; G06F 1/3265; G06F 3/14; Y02D 10/00; A61B 5/1118
See application file for complete search history.

(56) References Cited

U.S. PATENT DOCUMENTS

| 5,924,980 | A | 7/1999 | Coetzee |
|---|---|---|---|
| 6,882,955 | B1 | 4/2005 | Ohlenbusch et al. |
| 7,627,423 | B2 | 12/2009 | Brooks |
| 7,706,973 | B2 | 4/2010 | McBride et al. |
| 7,721,118 | B1 | 5/2010 | Tamasi et al. |
| 7,917,198 | B2 | 3/2011 | Ahola et al. |
| 7,938,752 | B1 | 5/2011 | Wang |
| 8,052,580 | B2 | 11/2011 | Saalasti et al. |
| 8,323,188 | B2 | 12/2012 | Tran |
| 8,328,718 | B2 | 12/2012 | Tran |
| 8,538,693 | B2 | 9/2013 | McBride et al. |
| 8,612,142 | B2 | 12/2013 | Zhang |
| 8,655,591 | B2 | 2/2014 | Van Hende |
| 8,781,730 | B2 | 7/2014 | Downey et al. |
| 8,848,058 | B2 * | 9/2014 | Ayer ........... A63B 24/0003 386/241 |
| 8,949,022 | B1 | 2/2015 | Fahrner et al. |
| 9,008,967 | B2 | 4/2015 | McBride et al. |
| 9,079,090 | B2 | 7/2015 | Hohteri |
| 9,107,586 | B2 | 8/2015 | Tran |
| 9,222,787 | B2 | 12/2015 | Blumenberg et al. |
| 9,317,660 | B2 | 4/2016 | Burich et al. |
| 9,595,187 | B2 | 3/2017 | Kotz et al. |
| 9,648,108 | B2 | 5/2017 | Granqvist et al. |
| 9,665,873 | B2 | 5/2017 | Ackland et al. |
| 9,829,331 | B2 | 11/2017 | McBride et al. |
| 9,830,516 | B1 | 11/2017 | Biswas et al. |
| 9,907,473 | B2 | 3/2018 | Tran |
| 9,923,973 | B2 | 3/2018 | Granqvist et al. |
| 10,135,905 | B2 * | 11/2018 | Chaudhri ........... G06F 3/0488 |
| 10,234,290 | B2 | 3/2019 | Lush et al. |
| 10,244,948 | B2 | 4/2019 | Pham et al. |
| 10,295,556 | B1 | 5/2019 | Paczkowski et al. |
| 10,327,673 | B2 | 6/2019 | Eriksson et al. |
| 10,415,990 | B2 | 9/2019 | Cho et al. |
| 10,433,768 | B2 | 10/2019 | Eriksson et al. |
| 10,515,990 | B2 | 12/2019 | Hung et al. |
| 10,634,511 | B2 | 4/2020 | McBride et al. |
| 10,816,671 | B2 | 10/2020 | Graham et al. |
| 2003/0038831 | A1 | 2/2003 | Engelfriet |
| 2003/0109287 | A1 | 6/2003 | Villaret |
| 2005/0070809 | A1 | 3/2005 | Acres |
| 2005/0086405 | A1 | 4/2005 | Kobayashi et al. |
| 2006/0068812 | A1 | 3/2006 | Carro et al. |
| 2006/0136173 | A1 | 6/2006 | Case, Jr. et al. |
| 2006/0255963 | A1 | 11/2006 | Thompson et al. |
| 2007/0156335 | A1 | 7/2007 | McBride et al. |
| 2007/0208544 | A1 | 9/2007 | Kulach et al. |
| 2007/0276200 | A1 | 11/2007 | Ahola et al. |
| 2008/0052493 | A1 | 2/2008 | Chang |
| 2008/0109158 | A1 | 5/2008 | Huhtala et al. |
| 2008/0136620 | A1 | 6/2008 | Lee et al. |
| 2008/0158117 | A1 | 7/2008 | Wong et al. |
| 2008/0214360 | A1 | 9/2008 | Stirling et al. |
| 2008/0294663 | A1 | 11/2008 | Heinley et al. |
| 2008/0318598 | A1 | 12/2008 | Fry |
| 2009/0047645 | A1 | 2/2009 | Dibenedetto et al. |
| 2009/0048070 | A1 | 2/2009 | Vincent et al. |
| 2009/0094557 | A1 | 4/2009 | Howard |
| 2009/0100332 | A1 | 4/2009 | Kanjilal et al. |
| 2009/0265623 | A1 | 10/2009 | Kho et al. |
| 2010/0099539 | A1 * | 4/2010 | Haataja ........... A63B 71/0622 482/8 |
| 2010/0167712 | A1 | 7/2010 | Stallings et al. |
| 2010/0187074 | A1 | 7/2010 | Manni |
| 2010/0257014 | A1 | 10/2010 | Roberts et al. |
| 2010/0313042 | A1 | 12/2010 | Shuster |
| 2011/0010704 | A1 | 1/2011 | Jeon et al. |
| 2011/0152695 | A1 | 6/2011 | Granqvist et al. |
| 2011/0218385 | A1 | 9/2011 | Bolyard et al. |
| 2011/0251822 | A1 | 10/2011 | Darley et al. |
| 2011/0252351 | A1 | 10/2011 | Sikora et al. |
| 2011/0281687 | A1 | 11/2011 | Gilley et al. |
| 2011/0283224 | A1 | 11/2011 | Ramsey et al. |
| 2011/0288381 | A1 | 11/2011 | Barthlomew et al. |
| 2011/0296312 | A1 | 12/2011 | Boyer et al. |
| 2011/0307723 | A1 | 12/2011 | Cupps et al. |
| 2012/0022336 | A1 | 1/2012 | Teixeira |
| 2012/0100895 | A1 | 4/2012 | Priyantha et al. |
| 2012/0109518 | A1 | 5/2012 | Huang |
| 2012/0116548 | A1 | 5/2012 | Goree et al. |
| 2012/0123806 | A1 | 5/2012 | Schumann et al. |
| 2012/0158289 | A1 | 6/2012 | Bernheim Brush et al. |
| 2012/0185268 | A1 | 7/2012 | Wiesner et al. |
| 2012/0219186 | A1 | 8/2012 | Wang et al. |
| 2012/0239173 | A1 | 9/2012 | Laikari et al. |
| 2012/0283855 | A1 | 11/2012 | Hoffman et al. |
| 2012/0289791 | A1 | 11/2012 | Jain et al. |
| 2012/0317520 | A1 * | 12/2012 | Lee ........... G06F 3/04817 715/863 |
| 2013/0053990 | A1 | 2/2013 | Ackland et al. |
| 2013/0060167 | A1 | 3/2013 | Dracup et al. |
| 2013/0095459 | A1 | 4/2013 | Tran |
| 2013/0127636 | A1 | 5/2013 | Aryanpur et al. |
| 2013/0151874 | A1 | 6/2013 | Parks et al. |
| 2013/0166888 | A1 | 6/2013 | Branson et al. |
| 2013/0178334 | A1 | 7/2013 | Brammer |
| 2013/0187789 | A1 | 7/2013 | Lowe |
| 2013/0190903 | A1 | 7/2013 | Balakrishnan et al. |
| 2013/0217979 | A1 | 8/2013 | Blackadar et al. |
| 2013/0225370 | A1 | 8/2013 | Flynt et al. |
| 2013/0234924 | A1 | 9/2013 | Janefalkar et al. |
| 2013/0250845 | A1 | 9/2013 | Greene et al. |
| 2013/0289932 | A1 | 10/2013 | Baechler et al. |
| 2013/0304377 | A1 | 11/2013 | Van Hende |
| 2013/0312043 | A1 | 11/2013 | Stone et al. |
| 2013/0332286 | A1 | 12/2013 | Medelius et al. |
| 2013/0345978 | A1 | 12/2013 | Lush et al. |
| 2014/0018686 | A1 | 1/2014 | Medelius et al. |
| 2014/0046223 | A1 | 2/2014 | Kahn et al. |
| 2014/0094200 | A1 | 4/2014 | Schatzberg et al. |
| 2014/0135593 | A1 | 5/2014 | Jayalth et al. |
| 2014/0142732 | A1 | 5/2014 | Karvonen |
| 2014/0149754 | A1 | 5/2014 | Silva et al. |
| 2014/0156084 | A1 * | 6/2014 | Rahman ........... G16H 40/67 700/275 |
| 2014/0159915 | A1 | 6/2014 | Hong et al. |
| 2014/0163927 | A1 | 6/2014 | Molettiere et al. |
| 2014/0164611 | A1 | 6/2014 | Molettiere et al. |
| 2014/0208333 | A1 | 7/2014 | Beals et al. |
| 2014/0218281 | A1 | 8/2014 | Amayeh et al. |
| 2014/0235166 | A1 | 8/2014 | Molettiere et al. |
| 2014/0237028 | A1 | 8/2014 | Messenger et al. |

(56) References Cited

U.S. PATENT DOCUMENTS

| | | |
|---|---|---|
| 2014/0257533 A1 | 9/2014 | Morris et al. |
| 2014/0275821 A1 | 9/2014 | Beckman |
| 2014/0288680 A1 | 9/2014 | Hoffman et al. |
| 2014/0300490 A1 | 10/2014 | Kotz et al. |
| 2014/0336796 A1 | 11/2014 | Agnew |
| 2014/0337036 A1 | 11/2014 | Haiut et al. |
| 2014/0337450 A1 | 11/2014 | Choudhary et al. |
| 2014/0343380 A1 | 11/2014 | Carter et al. |
| 2014/0350883 A1 | 11/2014 | Carter et al. |
| 2014/0365107 A1 | 12/2014 | Dutta et al. |
| 2014/0372064 A1 | 12/2014 | Darley et al. |
| 2015/0006617 A1 | 1/2015 | Yoo et al. |
| 2015/0037771 A1 | 2/2015 | Kaleal, III et al. |
| 2015/0042468 A1 | 2/2015 | White et al. |
| 2015/0057945 A1 | 2/2015 | White et al. |
| 2015/0113417 A1* | 4/2015 | Yuen .................. G16H 20/30 715/736 |
| 2015/0119198 A1 | 4/2015 | Wisbey et al. |
| 2015/0119728 A1 | 4/2015 | Blackadar et al. |
| 2015/0127966 A1 | 5/2015 | Ma et al. |
| 2015/0141873 A1 | 5/2015 | Fei |
| 2015/0160026 A1 | 6/2015 | Kitchel |
| 2015/0180842 A1 | 6/2015 | Panther |
| 2015/0185815 A1 | 7/2015 | Debates et al. |
| 2015/0209615 A1* | 7/2015 | Edwards ............ A61B 5/02438 482/9 |
| 2015/0233595 A1 | 8/2015 | Fadell et al. |
| 2015/0272483 A1 | 10/2015 | Etemad et al. |
| 2015/0312857 A1 | 10/2015 | Kim et al. |
| 2015/0317801 A1 | 11/2015 | Bentley et al. |
| 2015/0326709 A1 | 11/2015 | Pennanen et al. |
| 2015/0334772 A1 | 11/2015 | Wong et al. |
| 2015/0335978 A1 | 11/2015 | Syed et al. |
| 2015/0342533 A1 | 12/2015 | Kelner |
| 2015/0347983 A1 | 12/2015 | Jon et al. |
| 2015/0350822 A1 | 12/2015 | Xiao et al. |
| 2015/0362519 A1 | 12/2015 | Balakrishnan et al. |
| 2015/0374279 A1 | 12/2015 | Takakura et al. |
| 2015/0382150 A1 | 12/2015 | Ansermet et al. |
| 2016/0007288 A1 | 1/2016 | Samardzija et al. |
| 2016/0007934 A1 | 1/2016 | Arnold et al. |
| 2016/0012294 A1 | 1/2016 | Bouck |
| 2016/0018899 A1* | 1/2016 | Tu .................. G06F 1/3206 715/863 |
| 2016/0023043 A1 | 1/2016 | Grundy |
| 2016/0026236 A1 | 1/2016 | Vasistha et al. |
| 2016/0034043 A1 | 2/2016 | Le Grand et al. |
| 2016/0034133 A1 | 2/2016 | Wilson et al. |
| 2016/0041593 A1 | 2/2016 | Dharawat |
| 2016/0058367 A1 | 3/2016 | Raghuram et al. |
| 2016/0058372 A1 | 3/2016 | Raghuram et al. |
| 2016/0059079 A1 | 3/2016 | Watterson |
| 2016/0072557 A1 | 3/2016 | Ahola |
| 2016/0081028 A1 | 3/2016 | Chang et al. |
| 2016/0081625 A1 | 3/2016 | Kim et al. |
| 2016/0084869 A1 | 3/2016 | Yuen et al. |
| 2016/0091980 A1 | 3/2016 | Baranski et al. |
| 2016/0104377 A1 | 4/2016 | French et al. |
| 2016/0105852 A1 | 4/2016 | Papakipos et al. |
| 2016/0135698 A1* | 5/2016 | Baxi .................. A61B 5/7225 600/479 |
| 2016/0143579 A1 | 5/2016 | Martikka et al. |
| 2016/0144236 A1 | 5/2016 | Ko et al. |
| 2016/0148396 A1* | 5/2016 | Bayne .................. G09G 3/2003 345/593 |
| 2016/0148615 A1 | 5/2016 | Lee et al. |
| 2016/0184686 A1 | 6/2016 | Sampathkumaran |
| 2016/0209907 A1 | 7/2016 | Han et al. |
| 2016/0226945 A1 | 8/2016 | Granqvist et al. |
| 2016/0259495 A1* | 9/2016 | Butcher ............ G06F 3/04845 |
| 2016/0317097 A1 | 11/2016 | Adams et al. |
| 2016/0327915 A1 | 11/2016 | Katzer et al. |
| 2016/0328991 A1 | 11/2016 | Simpson et al. |
| 2016/0346611 A1 | 12/2016 | Rowley et al. |
| 2016/0367202 A1 | 12/2016 | Carter et al. |
| 2016/0374566 A1 | 12/2016 | Fung et al. |
| 2016/0379547 A1 | 12/2016 | Okada |
| 2017/0010677 A1* | 1/2017 | Roh .................. G06F 3/0488 |
| 2017/0011089 A1 | 1/2017 | Bermudez et al. |
| 2017/0011210 A1* | 1/2017 | Cheong .................. H04W 4/00 |
| 2017/0032256 A1 | 2/2017 | Otto et al. |
| 2017/0038740 A1 | 2/2017 | Knappe et al. |
| 2017/0043212 A1 | 2/2017 | Wong et al. |
| 2017/0063475 A1 | 3/2017 | Feng |
| 2017/0065230 A1 | 3/2017 | Sinha et al. |
| 2017/0087431 A1 | 3/2017 | Syed et al. |
| 2017/0124517 A1 | 5/2017 | Martin |
| 2017/0153119 A1 | 6/2017 | Nieminen et al. |
| 2017/0153693 A1 | 6/2017 | Duale et al. |
| 2017/0154270 A1 | 6/2017 | Lindman et al. |
| 2017/0168555 A1 | 6/2017 | Munoz et al. |
| 2017/0173391 A1 | 6/2017 | Wiebe et al. |
| 2017/0209743 A1 | 7/2017 | Bengtsson et al. |
| 2017/0228091 A1* | 8/2017 | Ogita .................. G06F 3/04886 |
| 2017/0232294 A1 | 8/2017 | Kruger et al. |
| 2017/0262699 A1 | 9/2017 | White et al. |
| 2017/0266494 A1 | 9/2017 | Crankson et al. |
| 2017/0316182 A1 | 11/2017 | Blackadar et al. |
| 2017/0340221 A1 | 11/2017 | Cronin et al. |
| 2018/0015329 A1 | 1/2018 | Burich et al. |
| 2018/0040290 A1* | 2/2018 | Liu .................. G04C 3/002 |
| 2018/0108323 A1 | 4/2018 | Lindman et al. |
| 2018/0193695 A1 | 7/2018 | Lee |
| 2018/0345077 A1 | 12/2018 | Blahnik et al. |
| 2019/0025928 A1 | 1/2019 | Pantelopoulos et al. |
| 2019/0056777 A1 | 2/2019 | Munoz et al. |
| 2019/0069244 A1 | 2/2019 | Jeon et al. |
| 2019/0367143 A1 | 12/2019 | Sinclair et al. |

FOREIGN PATENT DOCUMENTS

| | | |
|---|---|---|
| CN | 102495756 A | 6/2012 |
| CN | 103309428 A | 9/2013 |
| CN | 103631359 A | 3/2014 |
| CN | 103970271 A | 8/2014 |
| CN | 204121706 U | 1/2015 |
| CN | 104680046 A1 | 6/2015 |
| CN | 105242779 A1 | 1/2016 |
| CN | 105706093 A | 6/2016 |
| CN | 106062661 A | 10/2016 |
| CN | 106170247 A | 11/2016 |
| CN | 106604369 A | 4/2017 |
| CN | 106984025 A | 7/2017 |
| CN | 106999106 A | 8/2017 |
| CN | 108052272 A | 5/2018 |
| CN | 103154954 B | 6/2018 |
| CN | 108377264 A | 8/2018 |
| CN | 108983873 A | 12/2018 |
| EP | 1755098 A2 | 2/2007 |
| EP | 2096820 A1 | 9/2009 |
| EP | 2098165 A1 | 9/2009 |
| EP | 2107837 A1 | 10/2009 |
| EP | 2172249 A2 | 4/2010 |
| EP | 2770454 A1 | 8/2014 |
| EP | 2703945 A2 | 3/2015 |
| EP | 2849473 A1 | 3/2015 |
| EP | 2910901 A1 | 8/2015 |
| EP | 2996409 A1 | 3/2016 |
| EP | 3018582 A2 | 5/2016 |
| EP | 3023859 A1 | 5/2016 |
| EP | 3361370 A | 8/2018 |
| FI | 126911 B | 2/2017 |
| GB | 2404593 A | 2/2005 |
| GB | 2425180 A | 10/2006 |
| GB | 2513585 A | 11/2014 |
| GB | 2530196 A | 3/2016 |
| GB | 2537423 A | 10/2016 |
| GB | 2541234 A | 2/2017 |
| GB | 2555107 A | 4/2018 |
| KR | 20110070049 A | 6/2011 |
| KR | 101500662 B1 | 3/2015 |
| SE | 528295 C2 | 10/2006 |
| TW | 201706840 A | 2/2017 |

(56) References Cited

FOREIGN PATENT DOCUMENTS

| TW | I598076 A | 9/2018 |
|---|---|---|
| WO | WO02054157 A1 | 7/2002 |
| WO | WO2010083562 A1 | 7/2010 |
| WO | WO2010144720 A1 | 12/2010 |
| WO | WO2011061412 A1 | 5/2011 |
| WO | WO2011123932 A1 | 10/2011 |
| WO | WO2012037637 A1 | 3/2012 |
| WO | WO2012115943 A1 | 8/2012 |
| WO | WO2012141827 A2 | 10/2012 |
| WO | WO2013091135 A1 | 6/2013 |
| WO | WO2013121325 A2 | 8/2013 |
| WO | WO2014118767 A1 | 8/2014 |
| WO | WO2014144258 A2 | 9/2014 |
| WO | WO2014193672 A1 | 12/2014 |
| WO | WO2014209697 A1 | 12/2014 |
| WO | WO2015021407 A1 | 2/2015 |
| WO | WO2014182162 A3 | 6/2015 |
| WO | WO2015087164 A1 | 6/2015 |
| WO | WO2015131065 A1 | 9/2015 |
| WO | WO2016022203 A1 | 2/2016 |
| WO | WO2016037012 A1 | 3/2016 |
| WO | WO2017011818 A1 | 1/2017 |
| WO | WO2018217348 A1 | 11/2018 |
| WO | WO2018222936 A1 | 12/2018 |

OTHER PUBLICATIONS

Qualcomm Snapdragon Wear 3100 Platform Supports New Ultra-Low Power System Architecture For Next Generation Smartwatches. Qualcomm Technologies, Inc., Sep. 10, 2018, Retrieved on May 28, 2020 from: <https://www.qualcomm.com/news/releases/2018/09/10/qualcomm-snapdragon-wear-3100-platform-supports-new-ultra-low-power-system> sections "Snapdragon Wear 3100 Based Smartwatches Aim to Enrich the User Experience" on pp. 3-4.

CNET: Dec. 11, 2017, "Apple watch can now sync with a treadmill", youtube.com, [online], Available from: https://www.youtube.com/watch?v=7RvMC3wFDME [ Accessed Nov. 19, 2020].

Sheta et al: Packet scheduling in LTE mobile network. International Journal of Scientific & Engineering Research, Jun. 2013, vol. 4, Issue 6.

Cash: A guide to GPS and route plotting for cyclists. 2018. www.cyclinguk.org/article/guide-gps-and-route-plotting-cyclists.

Sieber et al: Embedded systems in the Poseidon MK6 rebreather. Intelligent Solutions in Embedded Systems, 2009, pp. 37-42.

Ainsworth et al: Parallel Error Detection Using Heterogeneous Cores. 48th Annual IEEE/IFIP International Conference on Dependable Systems and Networks (DSN), 2018, IEEE, 2018.

Davis: The Best Technical Diving Computers 2019. Feb. 7, 2019.

* cited by examiner

METHOD FOR CONTROLLING A DISPLAY

RELATED APPLICATIONS

This application is a continuation-in-part of U.S. patent application Ser. No. 15/784,234 filed on Oct. 16, 2017, which claims priority from both the Finnish patent application No. 20165790 filed on Oct. 17, 2016 and the British patent application No. 1617575.4 filed on Oct. 17, 2016, and U.S. patent application Ser. No. 16/228,981 filed on Dec. 21, 2018, which is a continuation in-part of U.S. patent application Ser. No. 15/382,763 filed on Dec. 19, 2016, which claims priority from both the Finnish patent application No. 20155989 filed on Dec. 21, 2015 and the British patent application No. 1522525.3 filed on Dec. 21, 2015, U.S. patent application Ser. No. 15/386,050 filed on Dec. 21, 2016 which claims priority from the Finnish patent application No. 20165707 filed on Sep. 20, 2016, U.S. patent application Ser. No. 15/386,062 filed on Dec. 21, 2016 which claims priority from the Finnish patent application No. 20165709 filed on Sep. 20, 2016, and U.S. patent application Ser. No. 15/386,074 filed on Dec. 21, 2016 which claims priority from the Finnish patent application No. 20165710 filed on Sep. 20, 2016. The subject matter of these is incorporated by reference in their entirety.

FIELD

Various example embodiments relate to controlling, e.g. activating and deactivating a display of a device.

BACKGROUND

Many people carry nowadays a wearable device, e.g. an activity tracker or a smart watch. Display of the device may cause excessive battery consumption in vain, if the display is unnecessarily in an activated state.

SUMMARY

According to some aspects, there is provided the subject-matter of the independent claims. Some embodiments are defined in the dependent claims. The scope of protection sought for various embodiments is set out by the independent claims. The embodiments, examples and features, if any, described in this specification that do not fall under the scope of the independent claims are to be interpreted as examples useful for understanding various embodiments.

According to a first aspect, an apparatus comprising at least one processor; and at least one memory including computer program code, the at least one memory and the computer program code configured to, with the at least one processor, cause the apparatus at least to perform: receiving an activity type of a user; receiving sensor data; determining at least one measurement value based on the sensor data; detecting at least one first activity type specific change in the at least one measurement value; and activating a display in response to detecting the at least one first activity type specific change in the at least one measurement value.

According to an embodiment, detecting the at least one first activity type specific change in the at least one measurement value comprises detecting a change in the measurement value; and comparing the detected change to an activity type specific reference value.

According to an embodiment, the activity type specific change is pre-learned.

According to an embodiment, the apparatus is caused to perform: receiving one or more user specific display activation rules; and updating the activity type specific reference value according to the one or more user specific display activation rules.

According to an embodiment, the apparatus is caused to perform receiving one or more user specific display activation rules; and activating the display further based on the one or more user specific display activation rules.

According to an embodiment, the apparatus is caused to perform detecting a second activity type specific change in the measurement value; and deactivating the display in response to detecting the second activity type specific change in the measurement value.

According to an embodiment, the activity type is a sport activity, daily use or sleeping.

According to an embodiment, the sensor data comprises one or more of acceleration sensor data, gyroscope data, altimeter data, heart rate sensor data, ambient light sensor data, and position sensor data.

According to an embodiment, the at least one measurement value is one or more of acceleration, velocity, distance, tilt, altitude, heart rate, ambient light, and location.

According to a second aspect, there is provided a method comprising receiving an activity type of a user; receiving sensor data; determining at least one measurement value based on the sensor data; detecting at least one first activity type specific change in the at least one measurement value; and activating a display in response to detecting the at least one first activity type specific change in the at least one measurement value.

Various embodiments of the second aspect may comprise at least one feature from the following bulleted list:
- detecting the at least one first activity type specific change in the at least one measurement value comprises detecting a change in the measurement value; and comparing the detected change to an activity type specific reference value
- the activity type specific change is pre-learned
- the method further comprises receiving one or more user specific display activation rules; and updating the activity type specific reference value according to the one or more user specific display activation rules
- the method further comprises receiving one or more user specific display activation rules; activating the display further based on the one or more user specific display activation rules
- the method further comprises detecting a second activity type specific change in the measurement value; and deactivating the display in response to detecting the second activity type specific change in the measurement value
- the activity type is a sport activity, daily use or sleeping
- the sensor data comprises one or more of acceleration sensor data, gyroscope data, altimeter data, heart rate sensor data, ambient light sensor data, and position sensor data
- the at least one measurement value is one or more of acceleration, velocity, distance, tilt, altitude, heart rate, ambient light, and location.

According to a third aspect, there is provided a non-transitory computer readable medium comprising program instructions that, when executed by at least one processor, cause an apparatus to at least to perform: receiving an activity type of a user; receiving sensor data; determining at least one measurement value based on the sensor data; detecting at least one first activity type specific change in the at least one measurement value; and activating a display in response to detecting the at least one first activity type specific change in the at least one measurement value.

According to a fourth aspect, there is provided a computer program configured to cause a method of the second aspect to be performed.

According to a fifth aspect, there is provided an apparatus comprising means for performing the method of the second aspect. The means comprises at least one processor; and at least one memory including computer program code, the at least one memory and the computer program code configured to, with the at least one processor, cause the performance of the apparatus.

DETAILED DESCRIPTION

Figure 1:
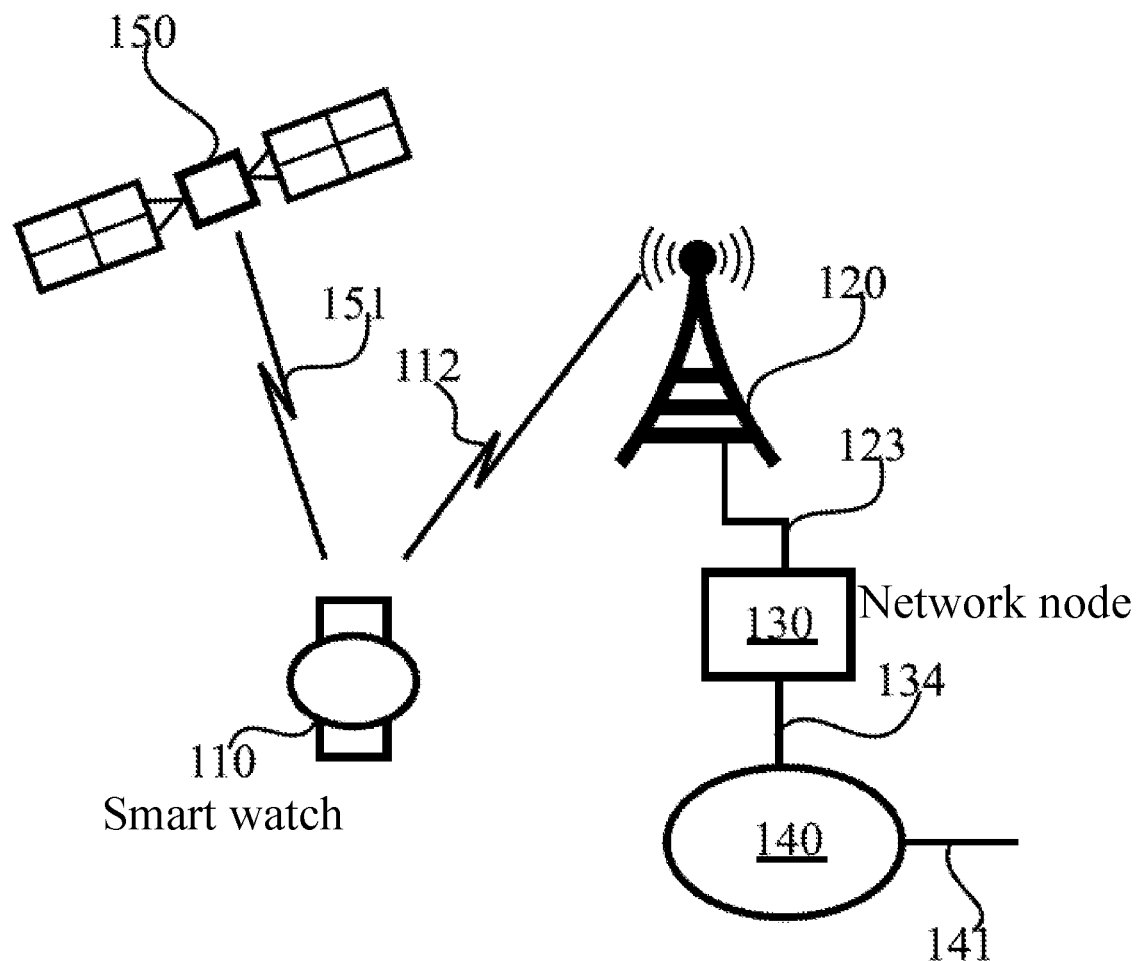
FIG. 1 shows, by way of example, a system.

FIG. 1 shows, by way of example, a system 100. The system comprises device 110, which may comprise, for example, a smart watch, digital watch, smartphone, phablet device, tablet device, or another type of suitable device. Device 110 may comprise a display, which may comprise a touchscreen display, for example. The display may be limited in size. Device 110 may be powered, for example, by a rechargeable battery. An example of a limited-size display is a display worn on a wrist.

Device 110 may be communicatively coupled with a communications network. For example, in FIG. 1 device 110 is coupled, via wireless link 112, with base station 120. Base station 120 may comprise a cellular or non-cellular base station, wherein a non-cellular base station may be referred to as an access point. Examples of cellular technologies include wideband code division multiple access, WCDMA, and long term evolution, LTE, while examples of non-cellular technologies include wireless local area network, WLAN, and worldwide interoperability for microwave access, WiMAX. Base station 120 may be coupled with network node 130 via connection 123. Connection 123 may be a wire-line connection, for example. Network node 130 may comprise, for example, a controller or gateway device. Network node 130 may interface, via connection 134, with network 140, which may comprise, for example, the Internet or a corporate network. Network 140 may be coupled with further networks via connection 141. In some embodiments, device 110 is not configured to couple with base station 120. Network 140 may comprise, or be communicatively coupled, with a back-end server, for example.

Device 110 may be configured to receive, from satellite constellation 150, satellite positioning information via satellite link 151. The satellite constellation may comprise, for example the global positioning system, GPS, or the Galileo constellation. Satellite constellation 150 may comprise more than one satellite, although only one satellite is illustrated in FIG. 1 for the same of clarity. Likewise, receiving the positioning information over satellite link 151 may comprise receiving data from more than one satellite.

Alternatively or additionally to receiving data from a satellite constellation, device 110 may obtain positioning information by interacting with a network in which base station 120 is comprised. For example, cellular networks may employ various ways to position a device, such as trilateration, multilateration or positioning based on an identity of a base station with which attachment is possible or ongoing. Likewise a non-cellular base station, or access point, may know its own location and provide it to device 110, enabling device 110 to position itself within communication range of this access point.

Device 110 may be configured to obtain a current time from satellite constellation 150, base station 120 or by requesting it from a user, for example. Once device 110 has the current time and an estimate of its location, device 110 may consult a look-up table, for example, to determine a time remaining until sunset or sunrise, for example. Device 110 may likewise gain knowledge of the time of year.

Device 110 may comprise, or be coupled with, at least one sensor, such as, for example, an acceleration sensor, altimeter, moisture sensor, temperature sensor, heart rate sensor, ambient light sensor, or a blood oxygen level sensor. Device 110 may be configured to produce and store, using the at least one sensor, sensor data, for example in a time series that comprises a plurality of samples taken in a time sequence.

The acceleration sensor, or motion sensor, may comprise e.g. a 6 degrees of freedom (DoF), or 9 DoF inertial measurement unit (IMU). The acceleration sensor may comprise e.g. a 3D digital accelerometer and a 3D digital gyroscope. A full-scale acceleration range of ±2±4±8±16 g and an angular rate range of ±125/±250/±500/±1000/±2000/±4000 degrees per second (dps) may be supported. The acceleration sensor may comprise a 3D magnetometer.

Device 110 may be configured to provide an activity session. An activity session may be associated with an activity type. The activity type may be a sport activity. Examples of activity types include rowing, paddling, cycling, jogging, walking, hunting, swimming and paragliding. In a simple form, an activity session may comprise device 110 storing sensor data produced with sensors comprised in device 110, or in another device with which device 110 is associated or paired. An activity session may be determined to have started and ended at certain points in time, such that the determination takes place afterward or concurrently with the starting and/or ending. In other words, device 110 may store sensor data to enable subsequent identification of activity sessions based at least partly on the stored sensor data.

An activity type may be determined based, at least partly, on the sensor data. This determining may take place when the activity is occurring, or afterwards, when analysing the sensor data. The activity type may be determined by device 110 or by a personal computer that has access to the sensor data, for example, or a server that is provided access to the sensor data. Where a server is given access to the sensor data, the sensor data may be anonymized. The determination of the activity type may comprise comparing the sensor data to reference data. The reference data may comprise reference datasets, each reference dataset being associated with an activity type. The determination may comprise determining the reference dataset that most resembles the sensor data, for example in a least-squares sense. Alternatively to the sensor data itself, a processed form of the sensor data may be compared to the reference data. The processed form may comprise, for example, a frequency spectrum obtained from the sensor data. Alternatively, the processed form may comprise a set of local minima and/or maxima from the sensor data time series. The determined activity type may be selected as the activity type associated with the reference dataset that most resembles the processed or original sensor data.

Different activity types may be associated with different characteristic frequencies. For example, acceleration sensor data may reflect a higher characteristic frequency when the user has been running, as opposed to walking. Thus the determination of activity type may be based, in some embodiments, at least partly, on deciding which reference dataset has a characteristic frequency that most closely matches a characteristic frequency of a section of the sensor-derived information time series under investigation. Alternatively or in addition, acceleration sensor data may be employed to determine a characteristic movement amplitude.

Where device 110 is configured to store a time series of more than one type of sensor data, plural sensor data types may be employed in determining the activity type. The reference data may comprise reference datasets that are multi-sensorial in nature in such a way, that each reference dataset comprises data that may be compared to each sensor data type that is available. For example, where device 110 is configured to compile a time series of acceleration and sound sensor data types, the reference data may comprise reference datasets, each reference dataset corresponding to an activity type, wherein each reference dataset comprises data that may be compared with the acceleration data and data that may be compared with the sound data. The determined activity type may be determined as the activity type that is associated with the multi-sensorial reference dataset that most closely matches the sensor data stored by device 110. Again, original or processed sensor data may be compared to the reference datasets. Where device 110 comprises, for example, a smartphone, it may comprise plural sensors to accomplish the smartphone function. Examples of such sensors comprise microphones to enable voice calls and cameras to enable video calls. Furthermore a radio receiver may, in some cases, be configurable to measure electric or magnetic field properties. Device 110 may comprise a radio receiver, in general, where device 110 is furnished with a wireless communication capability.

A first example of multi-sensorial activity type determination is hunting, wherein device 110 stores first-type sensor data that comprises acceleration sensor data and second-type sensor data that comprises sound data. The reference data would comprise a hunting reference dataset, which would comprise acceleration reference data and sound reference data, to enable comparison with sensor data stored by device 110. Hunting may involve periods of low sound and low acceleration and intermittent combinations of loud, short sound and a low-amplitude high-frequency acceleration corresponding to a gunshot sound and kick.

A second example of multi-sensorial activity type determination is swimming, wherein device 110 stores first-type sensor data that comprises moisture sensor data and second-type sensor data that comprises magnetic field data from a compass sensor. The reference data would comprise a swimming reference dataset, which would comprise moisture reference data and magnetic field reference data, to enable comparison with sensor data stored by device 110. Swimming may involve high moisture due to being immersed in water, and elliptical movements of an arm, to which device 110 may be attached, which may be detectable as periodically varying magnetic field data. In other words, the direction of the Earth's magnetic field may vary from the point of view of the magnetic compass sensor in a periodic way in the time series.

Overall, a determined, or derived, activity type may be considered an estimated activity type until the user has confirmed the determination is correct. In some embodiments, a few, for example two or three, most likely activity types may be presented to the user as estimated activity types for the user to choose the correct activity type from. Using two or more types of sensor data increases a likelihood the estimated activity type is correct.

A context process may be employed in deriving an estimated activity type based on sensor data. A context process may comprise first determining a context in which the sensor data has been produced. For example, the context process may comprise using the sensor data to determine the context, such as a user context, and then deriving an activity type within that context. For example, a context may comprise outdoor activity, and deriving an estimated activity type may comprise first determining, based on the sensor data, the user is in an outdoor context, selecting an outdoor-context machine readable instruction, and using the machine-readable instruction to differentiate between different outdoor-context activity types, such as jogging and orienteering. As another example, a context may comprise indoor activity, and deriving an estimated activity type may comprise first determining, based on the sensor data, the user is in an indoor context, selecting an indoor-context machine readable instruction, and using this machine-readable instruction to differentiate between different indoor activity types, such as 100 meter runs and wrestling.

The machine readable instruction may comprise, for example, a script, such as an executable or compilable script, an executable computer program, a software plugin or a non-executable computer-readable descriptor that enables device 110 to differentiate between at least two activity types within the determined context. The machine readable instruction may comprise indications as to which type or types of sensor data, and in which format, are to be used in deriving the activity type using the machine readable instruction.

Determining an outdoor context may comprise determining the sensor data indicates a wide range of geographic movement, indicating the user has roamed outdoors. Determining an indoor context may comprise determining the sensor data indicates a narrower range of geographic movement, indicating the user has remained within an small range during the activity session. Where temperature-type sensor data is available, a lower temperature may be associated with an outdoor activity and a higher temperature may be associated with an indoor activity. The temperature may be indicative of this in particular where the user is in a geographic area where winter, autumn or spring conditions cause an outdoor temperature to be lower than an indoor temperature. The geographic area may be available in positioning data.

Therefore, in some embodiments, deriving an estimated activity type is a two-phase process first comprising determining a context based on the sensor data, and then deriving an estimated activity type within that context, using a machine-readable instruction specific to that context. Selecting the context and/or the activity type within the context may comprise comparing sensor data, or processed sensor data, to reference data. The two-phase process may employ two types of reference data, context-type reference data and activity-type reference data, respectively.

Sensor data may be processed into a sequence of labels in order to determine the activity type. A sequence of labels may characterize the content of sensor data. For example, where the sensor data elements are numerical values obtained during jogging, a sequence of labels derived from those sensor data elements may comprise a sequence of labels: {jog-step, jog-step, jog-step, jog-step, jog-step, ... }. Likewise, where the sensor data elements are numerical values obtained during a long jump, a sequence of labels derived from those sensor data elements may comprise a sequence of labels: {sprint-step, sprint-step, sprint-step, sprint-step, sprint-step, leap, stop}. Likewise, where the sensor data elements are numerical values obtained during a triple jump, a sequence of labels derived from those sensor data elements may comprise a sequence of labels: {sprint-step, sprint-step, sprint-step, sprint-step, leap, leap, leap, stop}. The sequences of labels are thus usable in identifying the activity type, for example differentiating between long jump and triple jump based on the number of leaps.

The labels may be expressed in natural language or as indices to a pre-defined table, which may be dynamically updatable, as new kinds of exercise primitives become known. For example, in the table a jog-step may be represented as 01, a sprint-step (that is, a step in running much faster than jogging) as 02, a leap as 03, and a stopping of motion may be represented as 04. Thus the triple jump would be represented as a sequence of labels {02, 02, 02, 02, 03, 03, 03, 04}. The activity, for example a triple jump, may be detected from the labels, while the sequence of labels takes up significantly less space than the original sequences of sensor data elements.

To process the sequences of sensor data elements into a sequence of labels, sensor data segments may be derived from the sequences of sensor data elements. Each sensor data segment may then be associated with an exercise primitive and assigned a label, to obtain the sequence of labels. Each sensor data segment may comprise time-aligned sensor data element sub-sequences from at least two of the sequences of sensor data elements. In other words, segments of sensor data are derived, each such segment comprising a time slice of original sequences of sensor data elements. This may be conceptualized as time-slicing a multi-sensor data stream captured during jogging into the individual steps that make up the jogging session. Likewise other activity sessions may be time-sliced into exercise primitives which make up the activity.

To derive the segments, device 110 or another device may be configured to analyse the sequences of sensor data elements to identify therein units. Each segment may comprise slices of the sequences of sensor data elements, the slices being time-aligned, that is, obtained at the same time from the respective sensors.

For example, steps in running are repetitive in nature, wherefore identifying a pattern in the sequences of sensor data elements which repeats at a certain frequency is a clue the sequences may be segmented according to this frequency. A frequency may be identified, for example, by performing a fast fourier transform, FFT, on each of the sequences of sensor data elements, and then averaging the resulting spectrum, to obtain an overall frequency characteristic of the sequences of sensor data elements.

In case of motion, one way to segment the sensor data is to try to construct a relative trajectory of the sensor device. One way to estimate this trajectory is to double integrate the x-, y-, and z-components of acceleration sensor outputs. In this process one may remove gravity induced biases. Mathematically this can be done by calculating the baseline of each output. One way is to filter the data as in the next equation.

$$acc\_i\_baseline = acc\_i\_baseline + coeff\_a * (acc\_i - acc\_i\_baseline)$$

Acc above refers to the acceleration measurement and i refers to its components x, y, and z. These filtered values can be subtracted from the actual measurements: acc_i_without G=acc_i−acc_i_baseline. This is a rough estimate of the true linear acceleration, but still a fast and robust way to estimate it. The integration of these linear acceleration values leads to the estimate of the velocity of the sensor device in three-dimensional, 3D, space. The velocity components have biases due the incomplete linear acceleration estimate. These biases may be removed like in the previous equation:

$$v\_i\_baseline = v\_i\_baseline + coeff\_v * (v\_i - v\_i\_baseline)$$

V above refers to the velocity estimate and I refers to its components x, y, and z. These velocity components are not true velocities of the sensor device, but easily and robustly calculated estimates of them. The baseline components may be subtracted from the velocity estimates before integration: v_i_wo_bias=v_i−v_i_baseline. Since the method so far is incomplete, the integrals of the velocity components produce biased position estimates p_x, p_y, and p_z. Therefore these biases needs to be removed like in the previous equations:

$$p\_i\_baseline = p\_i\_baseline + coeff\_p * (p\_i - p\_i\_baseline)$$

P above refers to the position estimate and i refers to its components. Since this procedure effectively produces 0-mean values, the natural reference of position is p_x_ref=0, p_ref=0, and p_z_ref=0. The Euclidean distances of the measured values sqrt(p_x_ti2+p_y_ti2+p_z_ti**2) form a time series varying from 0 to some maximum value. ti refers to the index in the time series. These maximum values can detected easily. The moment in time of the maximum value starts and the next maximum value end the segment (and starts the next segment). The detection of the maximum value can be conditional i.e. the maximum value is accepted as a start/stop marker only when it exceeds a certain level.

Also, the above described procedure to calculate the relative trajectory can be more precise by utilizing the gyroscopes and using e.g. complementary filtering.

Other ways to segment the data, that is, derive the segments, may include fitting to a periodic model, using a suitably trained artificial neural network or using a separate segmenting signal provided over a radio or wire-line interface, for example. The segmenting signal may be correlated in time with the sequences of sensor data elements, to obtain the segments. A segmenting signal may be transmitted or provided by a video recognition system or pressure pad system, for example. Such a video recognition system may be configured to identify steps, for example.

Once the segments have been derived, each segment may be assigned a label. Assigning the label may comprise identifying the segment. The identification may comprise comparing the sensor data comprised in the segment to a library of reference segments, for example in a least-squares sense, and selecting from the library of reference segments a reference segment which most resembles the segment to be labelled. The label assigned to the segment will then be a label associated with the closest reference segment in the library of reference segments.

In some embodiments, a plurality of reference segment libraries is used, such that a first phase of the identification is selection of a reference segment library. For example, where two reference segment libraries are used, one of them could be used for continuous activity types and a second one of them could be used for discontinuous activity types. The continuous activity type is selected where the sequences of sensor data elements reflect a repetitive action which repeats a great number of times, such as jogging, walking, cycling or rowing. The discontinuous activity type is selected when the activity is characterized by brief sequences of action which are separated from each other in time, for example the afore-mentioned triple jump, or pole vault, being examples. Once the reference segment library is chosen, all the segments are labelled with labels from the selected reference segment library.

A benefit of first selecting a reference segment library is obtained in more effective labelling, as there is a lower risk segments are assigned incorrect labels. This is so, since the number of reference segments the sensor data segments are compared to is lower, increasing the chances a correct one is chosen.

Once the segments have been labelled, a syntax check may be made wherein it is assessed, if the sequence of labels makes sense. For example, if the sequence of labels is consistent with known activity types, the syntax check is passed. On the other hand, if the sequence of labels comprises labels which do not fit together, a syntax error may be generated. As an example, a sequence of jogging steps which comprises mixed therein a few paddling motions would generate a syntax error, since the user cannot really be jogging and paddling at the same time. In some embodiments, a syntax error may be resolved by removing from the sequence of labels the labels which do not fit in, in case they occur in the sequence of labels only rarely for example at a rate of less than 2%.

The reference segment libraries may comprise indications as to which labels fit together, to enable handling syntax error situations.

Different exercise primitives may be associated with different characteristic frequencies. For example, acceleration sensor data may reflect a higher characteristic frequency when the user has been running, as opposed to walking. Thus the labelling of the segments may be based, in some embodiments, at least partly, on deciding which reference segment has a characteristic frequency that most closely matches a characteristic frequency of a section of the sequence of sensor data elements under investigation. Alternatively or in addition, acceleration sensor data may be employed to determine a characteristic movement amplitude.

The reference segment libraries may comprise reference datasets that are multi-sensorial in nature in such a way, that each reference segment comprises data that may be compared to each sensor data type that is available. For example, where device 110 is configured to compile a time series of acceleration and sound sensor data types, the reference segments may comprise reference datasets, each reference segment corresponding to a label, wherein each reference segment comprises data that may be compared with the acceleration data and data that may be compared with the sound data, for example. The determined label may be determined as the label that is associated with the multi-sensorial reference segment that most closely matches the segment stored by device 110, for example. Device 110 may comprise, for example, microphones and cameras. Furthermore a radio receiver may, in some cases, be configurable to measure electric or magnetic field properties. Device 110 may comprise a radio receiver, in general, where device 110 is furnished with a wireless communication capability.

An example of activity type identification by segmenting and labelling is swimming, wherein device 110 stores sequences of sensor data elements that comprise moisture sensor data elements and magnetic field sensor data elements. The moisture sensor data elements indicating presence of water would cause a water-sport reference segment library to be used. Swimming may involve elliptical movements of an arm, to which device 110 may be attached, which may be detectable as periodically varying magnetic field data. In other words, the direction of the Earth's magnetic field may vary from the point of view of the magnetic field sensor in a periodic way in the time series. This would enable labelling the segments as, for example, breast-stroke swimming motions.

Overall, a determined, or derived, activity type may be considered an estimated activity type until the user has confirmed the determination is correct. In some embodiments, a few, for example two or three, most likely activity types may be presented to the user as estimated activity types for the user to choose the correct activity type from. Using two or more types of sensor data increases a likelihood the estimated activity type is correct. Once the user confirms or selects a specific activity type, labelling of segments may be enforced to be compliant with this activity type. This may mean, for example, that the set of reference segments the sensor data segments are compared to is limited to reference data segments consistent with this activity type.

Where device 110 or a personal device assigns the labels, the sequence of labels may be transmitted to a network server, for example, for storage. Device 110, the personal device or the server may determine an overall activity type the user is engaged in, based on the labels. This may be based on a library of reference label sequences, for example.

In general, device 110 or the personal device may receive a machine readable instruction, such as an executable program or executable script, from the server or another network entity. The machine readable instruction may be usable in determining activity type from the sequence of labels, and/or in assigning the labels to sensor data segments. In the latter case, the machine readable instruction may be referred to as a labelling instruction.

The process may adaptively learn, based on the machine readable instructions, how to more accurately assign labels and/or determine activity types. A server may have access to information from a plurality of users, and high processing capability, and thus be more advantageously placed to update the machine-readable instructions than device 110, for example.

The machine readable instructions may be adapted by the server. For example, a user who first obtains a device 110 may initially be provided, responsive to messages sent from device 110, with machine readable instructions that reflect an average user population. Thereafter, as the user engages in activity sessions, the machine readable instructions may be adapted to more accurately reflect use by this particular user. For example, limb length may affect periodical properties of sensor data captured while the user is swimming or running. To enable the adapting, the server may request sensor data from device 110, for example periodically, and compare sensor data so obtained to the machine readable instructions, to hone the instructions for future use with this particular user. Thus a beneficial effect is obtained in fewer incorrectly labelled segments, and more effective and accurate compression of the sensor data.

Figure 2A:
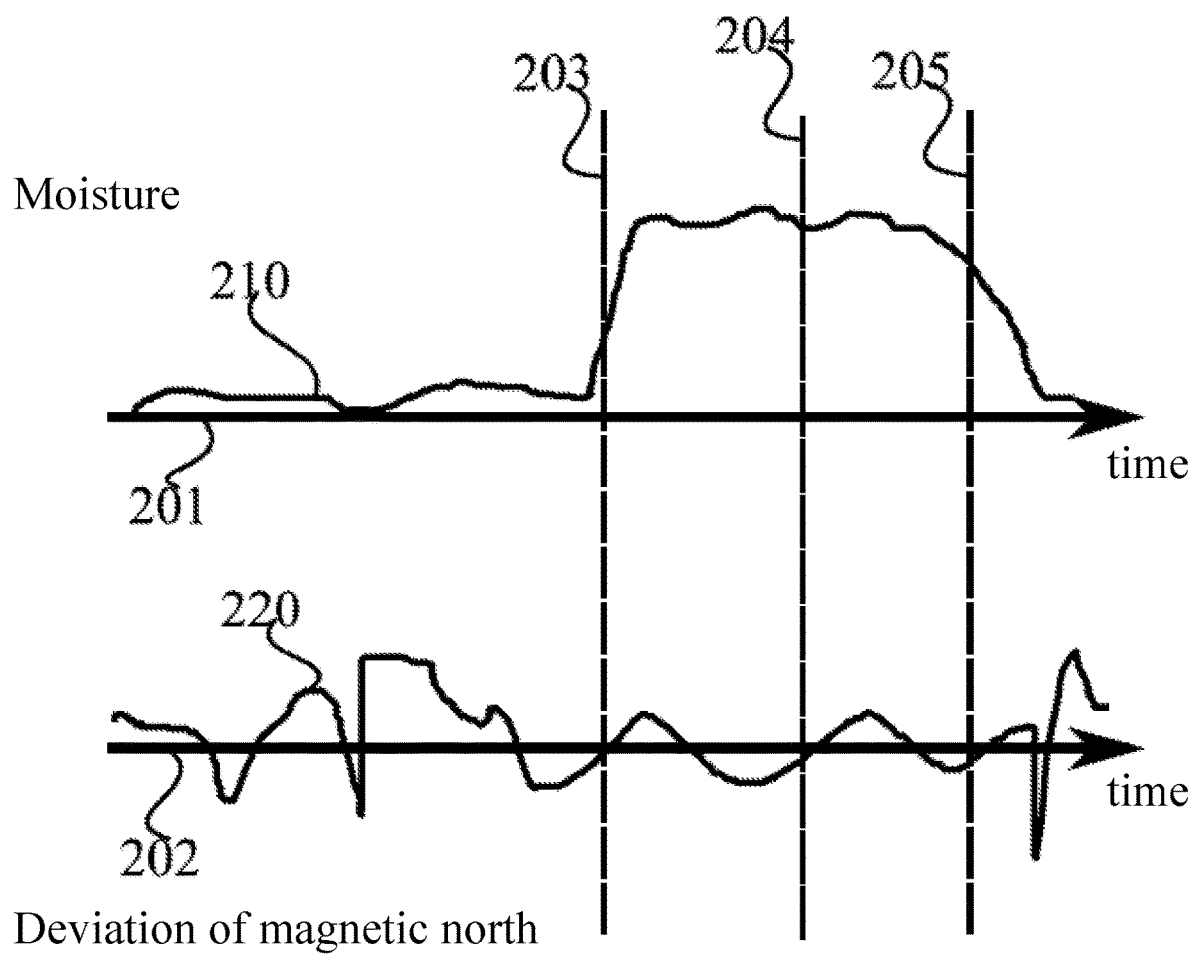
FIG. 2A illustrates an example of plural sequences of sensor data elements.

FIG. 2A illustrates an example of plural sequences of sensor data elements. On the upper axis, 201, is illustrated a sequence of moisture sensor data elements 210 while the lower axis, 202, illustrates a time series 220 of deviation of magnetic north from an axis of device 110, that is, a sequence of magnetic sensor data elements.

The moisture sequence 210 displays an initial portion of low moisture, followed by a rapid increase of moisture that then remains at a relatively constant, elevated, level before beginning to decline, at a lower rate than the increase, as device 110 dries.

Magnetic deviation sequence 220 displays an initial, erratic sequence of deviation changes owing to movement of the user as he operates a locker room lock, for example, followed by a period of approximately periodic movements, before an erratic sequence begins once more. The wavelength of the periodically repeating motion has been exaggerated in FIG. 2A to render the illustration clearer.

A swimming activity type may be determined as an estimated activity type, beginning from point 203 and ending in point 205 of the sequences. In detail, the sequences may be segmented into two segments, firstly from point 203 to point 204, and secondly from point 204 to point 205. As the moisture sensor indicates water sports, a water sports reference segment library is used to label the segments as, for example, freestroke swimming segments. The sequence of labels would thus be {freestroke, freestroke}. Of course, in actual swimming the number of segment would be much higher, but two segments are illustrated in FIG. 2A for the sake of simplicity. Overall, the two sensor data segments, from 203 to 204 and from 204 to 205, both comprise time-aligned sensor data element sub-sequences from sequences 210 and 220.

Figure 2B:
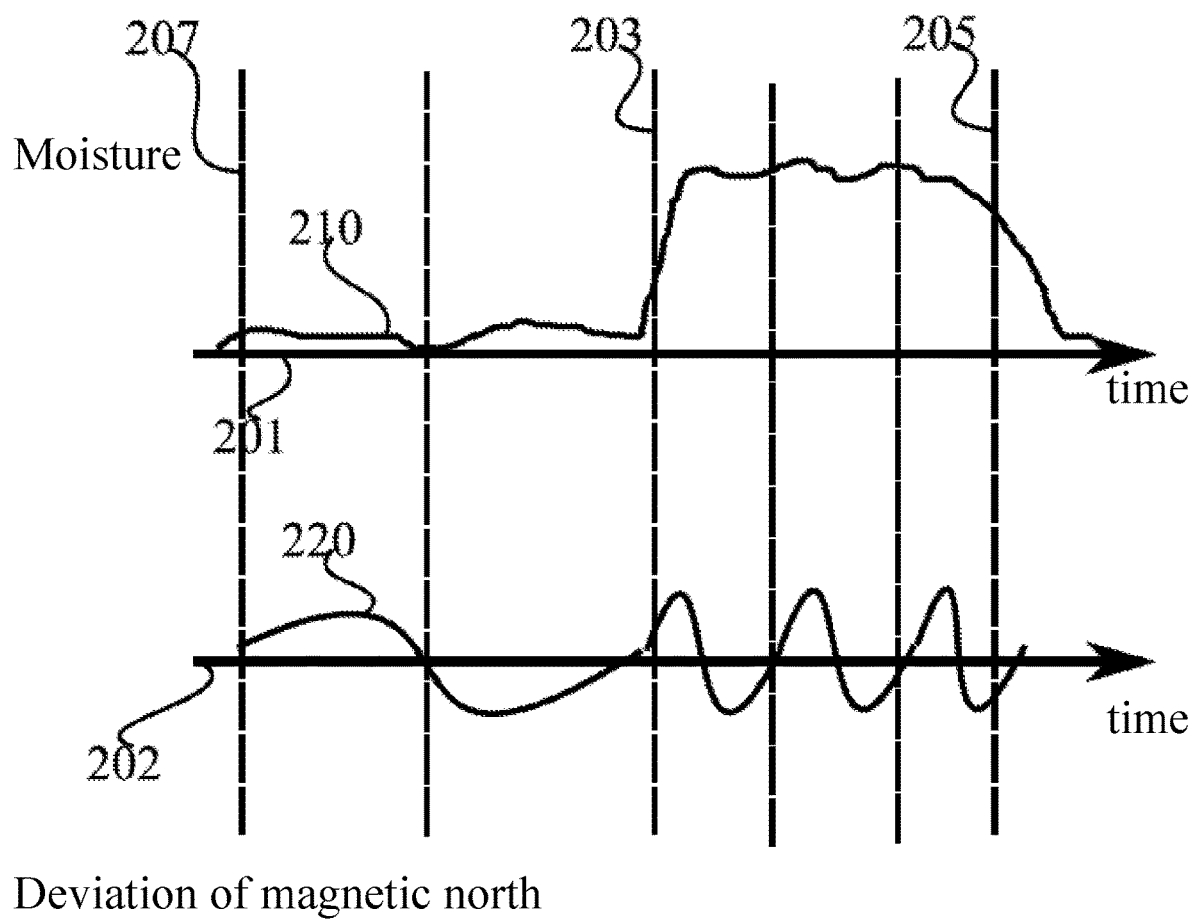
FIG. 2B illustrates a second example of plural sequences of sensor data elements.

FIG. 2B illustrates a second example of plural sequences of sensor data elements. In FIG. 2B, like numbering denotes like elements as in FIG. 2A. Unlike in FIG. 2A, not one but two activity sessions are determined in the time series of FIG. 2B. Namely, a cycling session is determined to start at beginning point 207 and to end at point 203, when the swimming session begins. Thus the compound activity session may relate to triathlon, for example. In cycling, moisture remains low, and magnetic deviation changes only slowly, for example as the user cycles in a velodrome. The segments would thus comprise two segments between points 207 and 203, and three segments between points 203 and 205. The sequence of labels could be {cycling, cycling, freestroke, freestroke, freestroke}. Again, the number of segments is dramatically reduced for the sake of clarity of illustration.

It may depend at least on the activity type, in which circumstances the user is interested to see the information displayed on the display of the device. The occasions where the user wants to see the displayed content may be associated with changes in received sensor data, such as acceleration sensor data and/or altimeter data.

Let us consider cycling as an activity type. The device may identify that the user is cycling, or the user may provide the activity type as input. Cycling may be identified e.g. based on acceleration sensor data and/or velocity data which may be derived e.g. from the acceleration sensor data or from positioning data such as GPS data. In cycling, the user may be interested to see information, e.g. heart rate, displayed on the display when cycling uphill. It may be detected based on the sensor data, e.g. altimeter data, that the altitude is changing. In response to detecting a pre-determined change in the sensor data, e.g. altitude of the user, a display may be activated. On a flat road, on the other hand, the user is not necessarily interested to see the display, and the display may be deactivated in order to save power. The device comprising the display and/or sensors, e.g. acceleration sensor, is not necessarily worn on the wrist of the user. The device may be attached to a bike of the user, e.g. to a handlebar of the bike.

The pre-determined change may be detected e.g. by comparing the sensor data, or a measurement value determined based on the sensor data, to a threshold value. The threshold value may be a pre-determined reference value. For example, if the measured quantity is altitude, and the measurement value is an altitude value, and if there is a small change in altitude, e.g. 2 m, the heart rate might not change much and the user might not be interested to see the heart rate. But if the change in altitude is above a pre-determined threshold, e.g. 10 m, the display may be activated. The change may be defined as a relative change e.g. as compared to an average altitude of a pre-determined distance preceding the measurement time point. As another example, the threshold may be set as a time period during which the altitude keeps increasing. It may be set that if the altitude increases for e.g. 5 seconds, the display may be activated.

Rules for activation of the display may be e.g. pre-determined. Alternatively, the system may adapt and learn the situations wherein the user wants to see the display. For example, the user may provide input to activate the display, e.g. via a button or a touchscreen. The system may detect based on the sensor data, e.g. altimeter data, that an uphill has started and the altitude increases for a pre-determined time. During uphill cycling, the user may provide input to activate the display. The system may detect that the user has activated the display many times in the same circumstances, i.e. during uphill cycling. A threshold value may be set for the number of times that the system has to detect the same behaviour in order to learn the rule for activation of the display. For example, if the same behaviour has repeated e.g. 3 times, the system may learn that the display is to be activated in those circumstances. Thus, the activity type specific change may be pre-learned.

There may be also user specific rules for activation of the display. For example, one user, e.g. a first user, may want to see the display during uphill as described above. Another user, e.g. a second user, may want to see the display when the uphill ends. If the system detects that the second user has activated pre-determined number of times the display by providing input when the uphill has ended, the system may learn a user specific rule for activation of the display. End of the uphill may be detected based on the sensor data, e.g. altimeter data, which does not change anymore, or starts decreasing if there is a downhill after the uphill.

Let us consider swimming as an activity type. The device may identify that the user is swimming, or the user may provide the activity type as input. When the user is swimming, the user may be unable to watch the display, e.g. on a wrist device. The user may be interested to see the display when the user stops swimming. It may be detected based on the sensor data, e.g. acceleration sensor data and/or moisture sensor data, that the user has stopped. In response to detecting a pre-determined change in the sensor data, e.g. the repetitive elliptical movement of the hands has ended, or velocity has changed to about zero, a display may be activated. During swimming, the display may be deactivated.

Rules for activation of the display may be e.g. pre-determined or learned by the system. For example, the user may provide input to activate the display at the end of the track after stopping swimming. The system may detect based on the sensor data, e.g. acceleration data, that the user has stopped swimming. The system may detect that the user has activated the display many times in the same circumstances, i.e. after a swimming session. A threshold value may be set for the number of times that the system has to detect the same behaviour in order to learn the rule for activation of the display. For example, if the same behaviour has repeated e.g. 3 times, the system may learn that the display is to be activated in those circumstances. Thus, the activity type specific change may be pre-learned.

A user specific rule for activation may be set for swimming. For example, a first user may want to see the display after a pre-determined swimming distance, e.g. after every 100 m. The user may want to quickly see the display without actually stopping swimming, and therefore, the rule based on the acceleration sensor data and stopping of swimming does not necessarily satisfy the needs of the first user. In this example, the pre-determined change in the measurement value corresponds to achieving a certain distance, i.e. the distance changes above a pre-defined threshold. The threshold value may be a pre-determined reference value. The display may be activated for a pre-determined time every 100 m, for example. A second user may want to see the display quickly, without actually stopping, after every 200 m. These different rules may be learned by the system and stored as part of a user profile, e.g. in a database such as a cloud based database. The swimming distance may be calculated based on turns at the ends of the pool. Turns may be detected based on acceleration sensor data. The length of the pool may be known. Also GPS data may be used for determining the swimming distance.

Let us consider cross-country skiing as an activity type. The device may identify that the user is skiing, or the user may provide the activity type as input. When the user is cross country skiing uphill, the user might not be interested to watch the display on the wrist device, since it may be difficult to keep the rhythm of poling. During downhill, on the other hand, it is easier to check the display. Thus, it may be detected based on the sensor data, e.g. acceleration sensor data and/or altimeter data, that the skier is skiing downhill. The skier may be e.g. in a typical downhill skiing position, i.e. in a tuck position. In response to a pre-determined change in the sensor data, a display may be activated. The change in the sensor data may be, e.g. that a movement of hands which is typical to skiing has stopped, and/or that the altitude is decreasing. During uphill skiing, the display may be deactivated in order to save power.

Rules for activation of the display may be e.g. pre-determined or learned by the system. For example, the user may provide input to activate the display after taking the tuck position for downhill. The system may detect based on the sensor data, that the user has taken the tuck position for downhill. The system may detect that the user has activated the display many times in the same circumstances. A threshold value may be set for the number of times that the system has to detect the same behaviour in order to learn the rule for activation of the display. For example, if the same behaviour has repeated e.g. 3 times, the system may learn that the display is to be activated in those circumstances. Thus, the activity type specific change may be pre-learned.

During cross-country skiing, or other outdoor sport in cold weather, the user may be assumed to wear gloves. It may be determined based on ambient light sensor data whether the wrist device is worn under the gloves or sleeve. Then, the system may determine that when the device is under the gloves, or other clothes, the display may be deactivated to save power. When the user is moving a cloth in order to see the display of the wrist device, the ambient light sensor may detect light. A change in the sensor data in this situation is a change in the amount of light. Then, the display may be activated in response to detecting the change in the sensor data.

Let us consider a ball game, e.g. floorball or football, as an activity type. The device may identify that the user is playing the ball game, or the user may provide the activity type as input. When the user is playing, the user may need to be focused on a ball or other players in the field, and therefore, might not be interested to watch the display on the wrist device. Thus, the display may be deactivated when the game is on-going. The game being on-going may be detected by the device e.g. based on sensor data, e.g. acceleration sensor data, which may indicate high frequency running, e.g. followed by a shoot with a stick. The shoot may be recognized by a derived trajectory of the hand, which may be calculated based on the acceleration sensor data. If the player has a break in the game, he may be interested to see the display. The break may be detected based on the sensor data, e.g. acceleration sensor data and/or velocity derived from the acceleration sensor data.

Rules for activation of the display may be e.g. pre-determined or learned by the system. For example, the user may provide input to activate the display when sitting on the player's bench. The user may want to follow his/her recovery and see the heart rate that should decrease. The system may detect that the user has activated the display many times in the same circumstances. A threshold value may be set for the number of times that the system has to detect the same behaviour in order to learn the rule for activation of the display. For example, if the same behaviour has repeated e.g. 3 times, the system may learn that the display is to be activated in those circumstances. Thus, the activity type specific change may be pre-learned.

Figure 3:
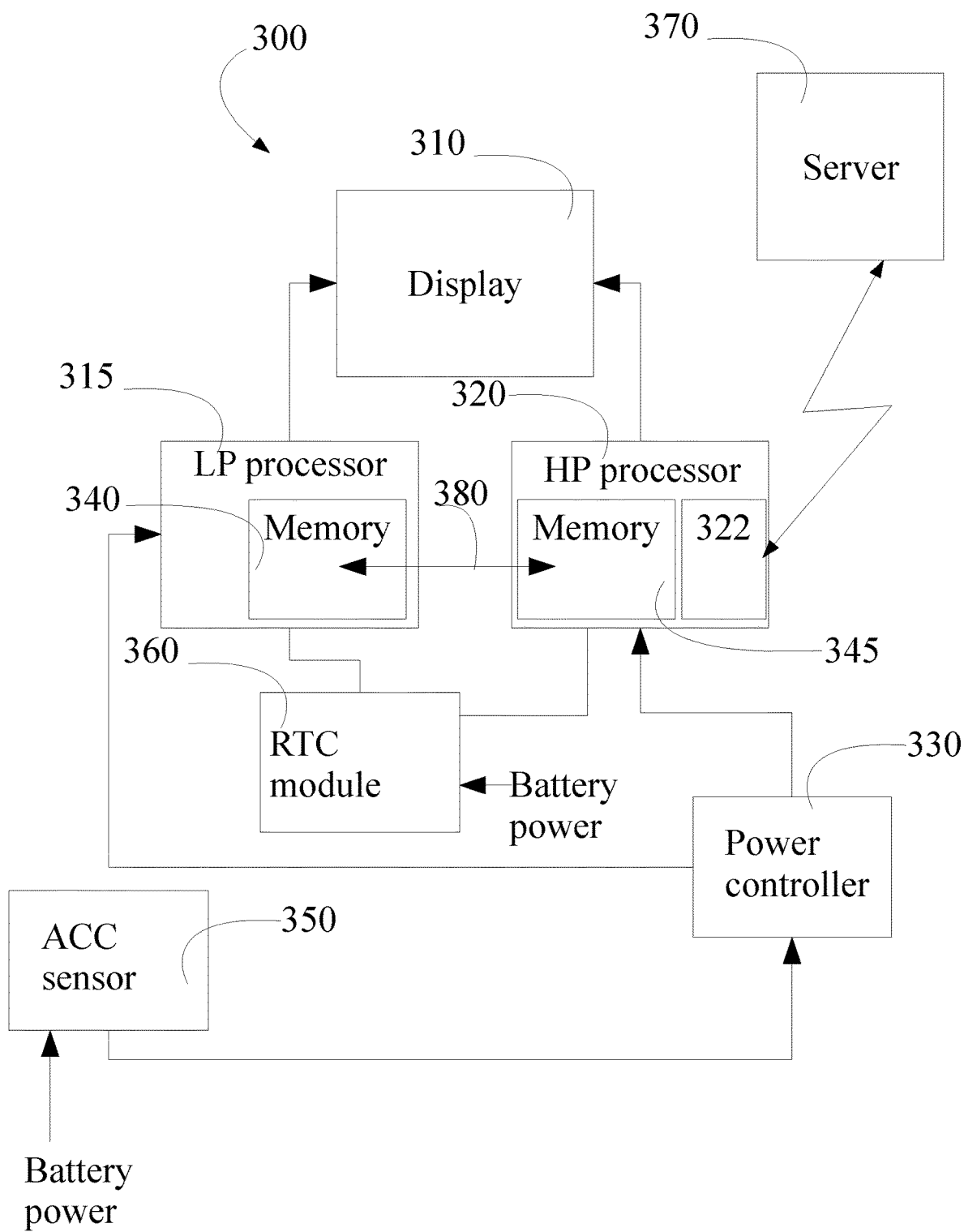
FIG. 3 shows, by way of example, a block diagram of a device.

Activation and deactivation of the display may be performed by the processor(s) of the device. FIG. 3 shows, by way of example, a block diagram of a device 300. The device may be e.g. a smart watch. The device comprises a display 310. The display may be e.g. a touchscreen display. Device 300 may comprise processing unit(s), e.g. two or more processing units, e.g. a low power (LP) processor 315 and a high power (HP) processor 320. The two or more processing units may each comprise a processing core. Each processing unit may comprise one or multiple uniformal or heterogeneous processor cores and/or different volatile and non-volatile memories. For example, device 300 may comprise a microprocessor with at least one processing core, and a microcontroller with at least one processing core. The processing cores may be of different type. For example, a processing core in a microcontroller may have more limited processing capability and/or a less capable memory technology than a processing core comprised in a microprocessor. In some embodiments, a single integrated circuit comprises two processing cores, a first one of which has lesser processing capability and consumes less power, and a second one of which has greater processing capability and consumes more power. In general a first one of the two processing units may have lesser processing capability and consume less power, and a second one of the two processing units may have greater processing capability and consume more power. Each of the processing units, e.g. the LP processor 315 and the HP processor 320, may be enabled to control the display 310 of device 300. The more capable processing unit may be configured to provide a richer visual experience via the display. The less capable processing unit may be configured to provide a reduced visual experience via the display. An example of a reduced visual experience is a reduced colour display mode, as opposed to a rich colour display mode. An another example of a reduced visual experience is one which is black-and-white. An example of a richer visual experience is one which uses colours. Colours may be represented with 16 bits or 24 bits, for example.

Each of the two processing units may comprise a display interface configured to communicate towards the display. For example, where the processing units comprise a microprocessor and a microcontroller, the microprocessor may comprise transceiver circuitry coupled to at least one metallic pin under the microprocessor, the at least one metallic pin being electrically coupled to an input interface of a display control device. The display control device, which may be comprised in the display, is configured to cause the display to display information in dependence of electrical signals received in the display control device. Likewise the microcontroller in this example may comprise transceiver circuitry coupled to at least one metallic pin under the microcontroller, the at least one metallic pin being electrically coupled to an input interface of a display control device. The display control device may comprise two input interfaces, one coupled to each of the two processing units, or alternatively the display control device may comprise a single input interface into which both processing units are enabled to provide inputs via their respective display interfaces. Thus a display interface in a processing unit may comprise transceiver circuitry enabling the processing unit to transmit electrical signals toward the display.

One of the processing units, for example the less capable or the more capable one, may be configured to control, at least in part, the other processing unit. For example, the less capable processing unit, for example a less capable processing core, may be enabled to cause the more capable processing unit, for example a more capable processing core, to transition into and from a hibernating state. These transitions may be caused to occur by signalling via an inter-processing unit interface, such as for example an inter-core interface.

The LP processor and the HP processor may be controlled by a power controller 330. The power controller controls the clock frequency of the processors. When transitioning into a hibernating state, or deactivated state, from an active state, the transitioning processing unit may store its context, at least in part, into a memory, such as for example a pseudo-static random access memory, PSRAM, SRAM, FLASH or ferroelectric RAM, FRAM. For example, the both processors, the LP processor 315 and the HP processor 320 may be shut down, and the context may be stored in memory 340, 345. If the LP processor and the HP processor are shut down, the display is deactivated and the power consumption is reduced, e.g. to the lowest possible power consumption. When transitioning from a hibernated state using a context stored in memory, a processing unit may resume processing faster and/or from a position where the processing unit was when it was hibernated. This way, a delay experienced by a user may be minimised. Alternative terms occasionally used for context include state and image. In a hibernating state, a clock frequency of the processing unit and/or an associated memory may be set to zero, meaning the processing unit is powered off and does not consume energy. Circuitry configured to provide an operating voltage to at least one processing unit may comprise a power management integrated circuit, PMIC, for example. Since device 300 comprises another processing unit, the hibernated processing unit may be powered completely off while maintaining usability of device 300.

Even if both processors, the LP processor and the HP processor, are shut down, the device is able to perform measurements during the activity session. For example, the acceleration sensor 350 comprises processor(s), and may be able to perform measurements continuously with low power consumption, and control the power controller 330. The acceleration sensor 350 may be provided with battery power.

The processing core(s) may be left in a reduced operation mode, if the activity and/or context is deemed to require a fast wakeup of the core. Wakeup from a state of hibernation, or full shut down, will take longer.

When transitioning from a hibernated state to an active state, the transitioning processing unit may have its clock frequency set to a non-zero value. The transitioning processing unit may read a context from a memory, wherein the context may comprise a previously stored context, for example a context stored in connection with transitioning into the hibernated state, or the context may comprise a default state or context of the processing unit stored into the memory in the factory. The memory may comprise pseudo-static random access memory, SRAM, FLASH and/or FRAM, for example. The memory used by the processing unit transitioning to and from the hibernated state may comprise DDR memory, for example.

The context shown on the display may comprise activity related, or performance related, information relating to the activity of the user. The displayed information may comprise at least one or more measurement values of e.g. heart rate, distance, velocity, location etc. The context, e.g. heart rate value, distance, velocity, location etc. may be updated in response to the activation of the display. One or more sensors may provide information to at least one of the processors. For example, a GPS sensor may provide location information to at least one of the processing cores to enable the device to determine its location.

Information shown on the display may comprise a thematic map, for example a heat map, which may be compiled to cover a geographic area. Users may engage in an activity session while in the geographic area. Activity types of such an activity session may comprise e.g. jogging, swimming, cycling, etc. When a user wishes to engage in an activity session of one's own, one's device may determine a route for this activity session based at least in part on a thematic map database. Determining the route may comprise designing the route, optionally based partly on user settings, based on where other users have engaged in activity sessions of the same type in the past. For example, a jogging route may be determined based, at least partly, on indications where other users have jogged in the past. Thematic maps may be downloaded from a server 370 through a communication interface 322.

The processor may produce a reduced version of the thematic map, or the reduced maps may be downloaded from the server 370 on demand. The demand may be based on the type of the device, the preferences of the user and/or the location of the user. The server may provide appropriate selection of activities for downloading. With a "reduced" map is here meant a reduced version of a thematic map. This may for example mean one or several of the following: less or no colours, lesser display resolution, slower display updates, reduced content, etc. Reduced thematic maps may be downloaded from the server 370, or they may be produced by the first processing core 320 and stored in its memory 345. In a two-processing core embodiment, the image(s) of the reduced thematic map may be copied (arrow 380) to a memory 340 of the low-power second processing core 315, to be provided as a reduced visual experience via the display.

The device may comprise a Real Time Clock (RTC) module 360. When the processors, e.g. the LP processor and the HP processor, are shut down, the RTC module may still be running. The RTC module, or RTC unit, may be a separate unit provided with battery power. The processing cores, e.g. the LP processor and the HP processor may then be completely shut off. RTC units may also be integrated in either one of the processors 315 or 320, or in both, but would then require at least some hardware around the processor in question to be powered up, with a power consumption of a few microamperes. Which alternative RTC units to use is a matter of a design choice. The RTC unit may trigger the processors at pre-defined time intervals to update the context, for example location. As another example, the RTC unit may start a processing core if a relatively long time has passed since the user last made an attempt to look at the display. In those situations, the user might no longer be interested in looking a display image previously stored in the memory which probably does not show correct context, e.g. correct location and/or activity of the user, anymore. Instead of just fetching for display a stored context, which may be outdated, a time delay since the last display action may be used as an indicator that the context has probably changed. As the RTC unit reveals this time delay, the information may be used for example to activate a GPS sensor in order to check the location and start at least one processor, e.g. the LP processor, to update the context of the user. Context dependent images may be fetched from a memory using a low-dropout (LDO) regulator as the power source for a hibernating processing core. The LDO regulator provides a fast wakeup. The stored images may be transferred directly from a memory to the display. The memory may be an internal memory 340, 345, or an external memory.

It may be determined based on current time provided by the RTC module 360 that it is night time and the user is usually sleeping. Sleeping may be considered as an activity type. User may also provide input for the device that the current activity type is sleeping. It may be confirmed based on sensor data that it is e.g. dark (based on ambient light sensor data) and/or the user is not moving (based on motion sensor data) or is moving very little, e.g. when changing position on bed. Then, it may be determined that the display may be deactivated and kept deactivated during sleeping time. Even if movement is detected based on sensor data, e.g. acceleration sensor data, the display may be kept deactivated. For example, the display may be kept deactivated, if the detected movement is below a pre-defined threshold. The threshold value may be a pre-determined reference value. It may be further set up that during sleeping time the display is kept deactivated even if the user is standing up and walking. This way no disturbing light from the display is emitted towards user's eyes. Further, the power is saved, since the display is not activated in vain.

However, the system may learn user specific rules for activation during sleeping. A user may want to see the display during sleeping time. The user may provide input to activate the display. The user may activate the display by user input, e.g. pushing a button or touching a touchscreen. The system may detect that the user has activated the display when waking up at night, and tilted the wrist such that the display is towards the user's face. Then, a user specific rule may be determined that even if it is night time, or sleeping time, the display is activated if a tilt of the wrist or a trajectory corresponding to bringing the watch towards the face is detected based on sensor data, e.g. acceleration sensor data.

Triggering events for causing the power controller 330 to control the processor(s) to activate and/or deactivate the display may be based, at least, on sensor data, e.g. acceleration sensor 350 data. In addition, current time data may be used for controlling the display. Different occasions for activation and/or deactivation of the display have been described above in the context of different activity types. What is common for these examples, a change in the measurement value derived from sensor data is detected. For example, an activity type specific change may be detected. In order to speed up the wakeup of hibernating, or shut down, processing core(s), their power supplies, e.g. a switched-mode power supply (SMPS), may be left on. Another exemplary way is to switch the SMPS off and connect a low dropout (LDO) regulator as a fast power source for the hibernating, or shut down, processing core in parallel over the SMPS.

If the device is set on a table, the display may be deactivated. It may be detected based on sensor data, e.g. acceleration sensor data, that the device is on a table, i.e. a flat surface. When the device is on a table, no motion is detected, so the change in the sensor data is stopping of motion.

The system may learn activation rules of the display also during daily use when the user is not performing a sport activity. Daily use without a sport activity or sport performance may be considered as an activity type. Activity type being daily use without sport activity may be determined e.g. based on sensor data, based on input by the user, or based on knowledge that the user is not currently recording any sport performance. For example, the user may wear a device on a wrist, and the display of the device may be deactivated. When the display is deactivated, the processors(s) controlling the display may be shut down. The user may provide input to activate a display after tilting the wrist such that the display of the device is towards user's face. The system may detect that the user has activated the display many times, e.g. a pre-determined number of times, after a similar tilt of the device. Then, the system learns to activate the display in response to detecting a pre-determined change in the sensor data. The change may be e.g. a tilt of the device. The tilt may be detected based on the sensor data, e.g. acceleration data.

When the activity type is walking or jogging, the display may be activated in response to detecting that the wrist is tilted such that the display of the device is towards user's face.

Figure 4:
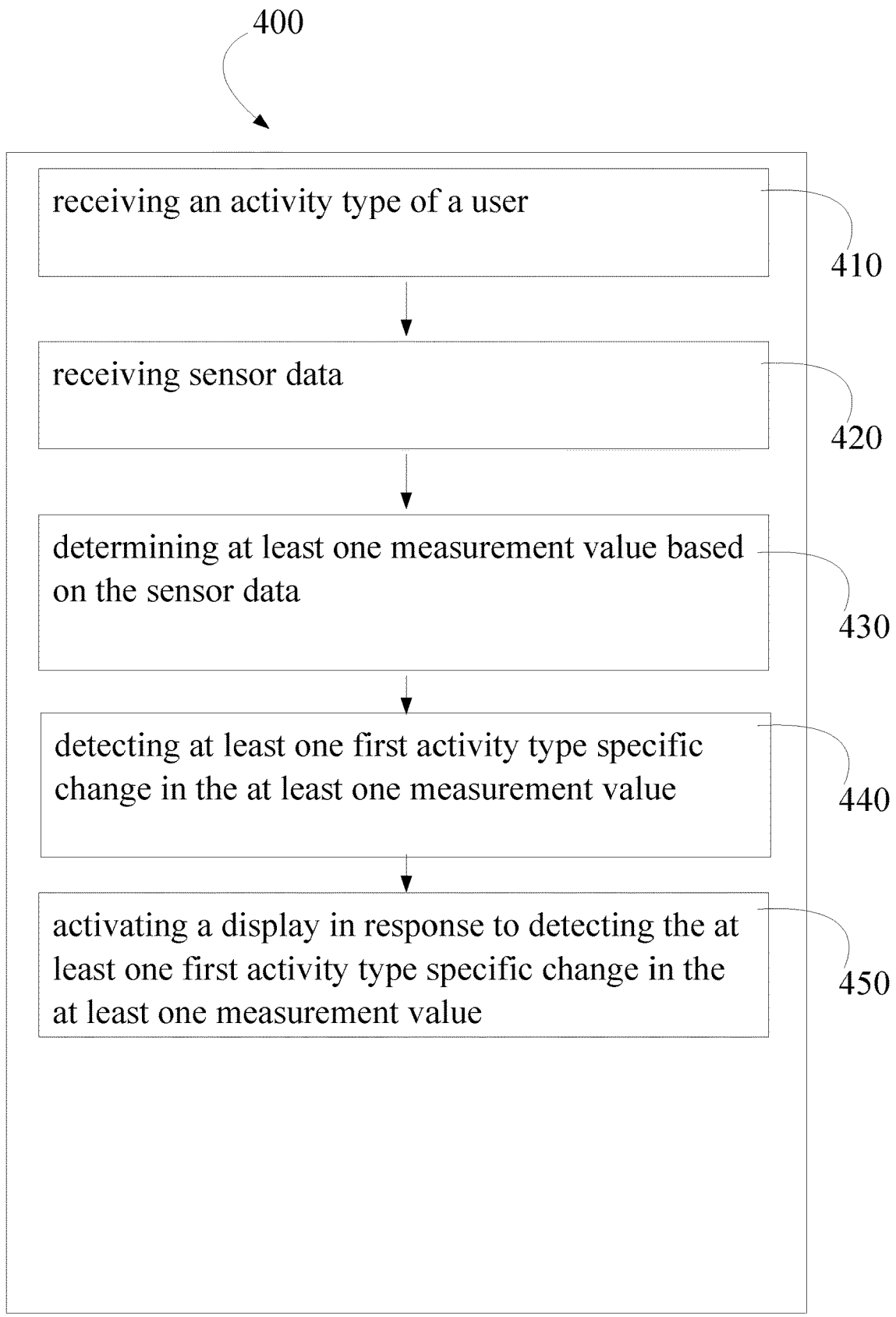
FIG. 4 shows, by way of example, a flow chart of a method for activating a display.

FIG. 4 shows, by way of example, a flow chart of a method for activating a display. The method 400 comprises receiving 410 an activity type of a user. The method 400 comprises receiving 420 sensor data. The method 400 comprises determining 430 at least one measurement value based on the sensor data. The method 400 comprises detecting 440 at least one first activity type specific change in the at least one measurement value. The method 400 comprises activating 450 a display in response to detecting the at least one first activity type specific change in the at least one measurement value.

The sensor data may comprise e.g. one or more of acceleration sensor data, gyroscope data, altimeter data, heart rate sensor data, ambient light sensor data, and position sensor data.

The measurement value of a measured quantity may be e.g. one or more of acceleration, velocity, distance, tilt, altitude, heart rate, ambient light, and location.

The activity type may be a sport activity, daily use or sleeping. The sport activity may be e.g. cycling, cross-country skiing, indoor games, jogging or walking.

The method provides more accurate activation of a display in the situations where the user is interested to see the information displayed on the display. Those situations may be determined based on the sensor data. In addition, those situations may be determined based on the activity type. This will result in more efficient power consumption, since the display is not activated in vain. Since the display is deactivated when the user is not interested to see the information displayed on the display, battery is saved. The method enables preventing false positives and false negatives relating to some activation and/or deactivation methods.

Figure 5A:
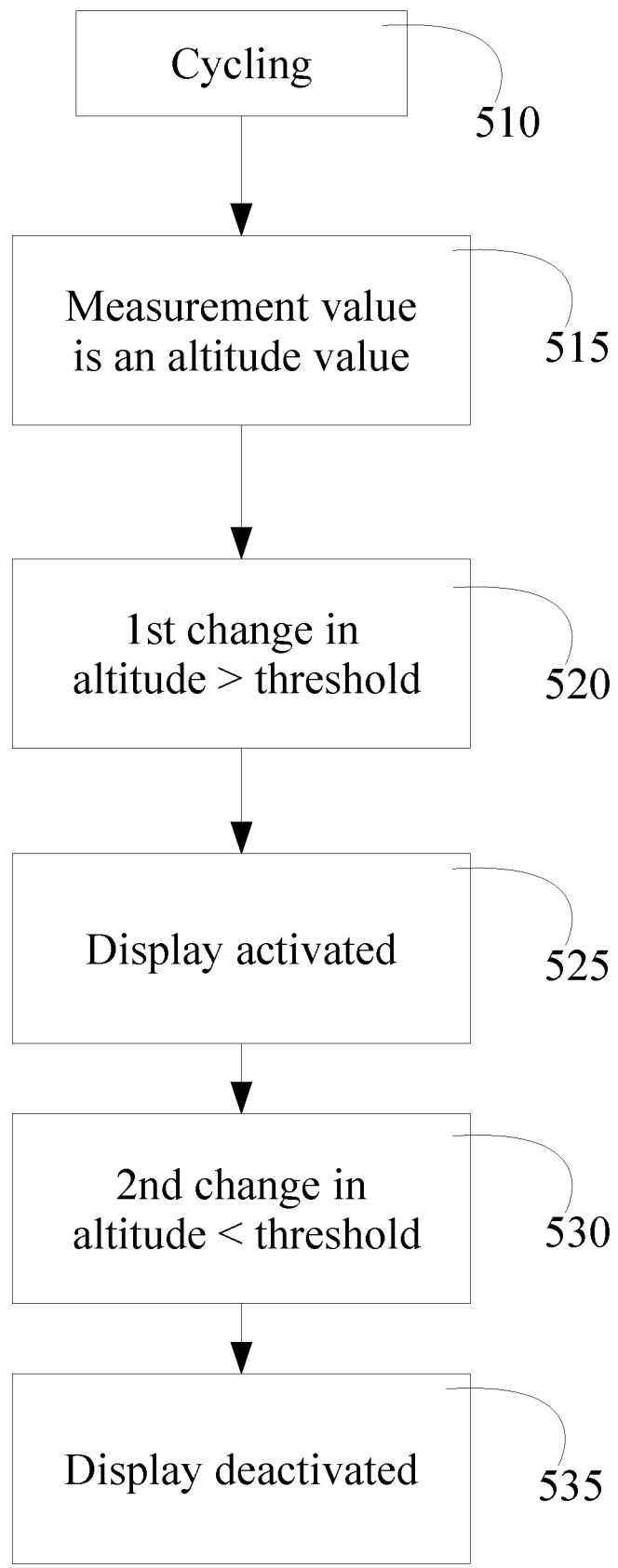
FIG. 5A shows, by way of example, a flow chart of display activation and deactivation relating to an activity type.
Figure 5B:
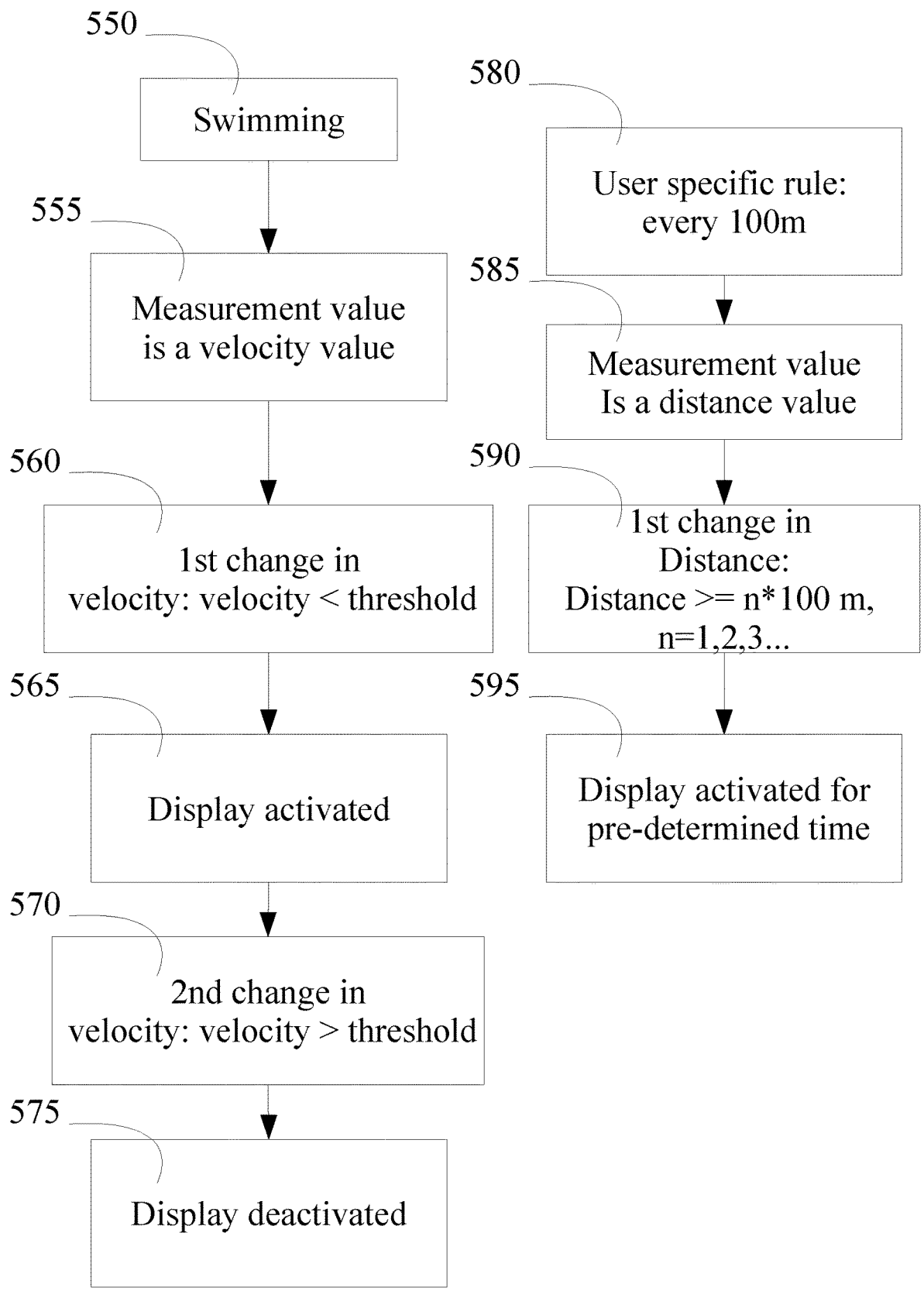
FIG. 5B shows, by way of example, a flow chart of display activation and deactivation relating to an activity type.

FIG. 5A and FIG. 5B show, by way of examples, flow charts of display activation and deactivation relating to different activity types, e.g. cycling 510 and swimming 550. It may be determined that the user is cycling, e.g. based on user input or based on sensor data, as described above. Sensor data is received during the activity. At least one measured quantity is altitude, and the measurement value is an altitude value 515. A first activity type specific change in the measurement value is detected, e.g. it may be detected that the change in the altitude is above a pre-defined threshold 520. In response to detecting the first activity type specific change in the measurement value, the display is activated 525. Then, a second activity type specific change in the measurement value is detected, e.g. it may be detected that the change in the altitude is below a pre-defined threshold 530. In response to detecting the second activity type specific change in the measurement value, the display is deactivated 535.

Referring to FIG. 5B, it may be determined that the user is swimming, e.g. based on user input or based on sensor data, as described above. Sensor data is received during the activity. At least one measurement quantity is velocity, and the measurement value is a velocity value 555. A first activity type specific change in the measurement value is detected, e.g. it may be detected that the velocity drops below a pre-determined threshold 560. In response to detecting the first activity type specific change in the measurement value, the display is activated 565. Then, a second activity type specific change in the measurement value is detected, e.g. it may be detected that the velocity is above a pre-determined threshold 570. In response to detecting the second activity type specific change in the measurement value, the display is deactivated 575. In addition, a user specific rule may be received. For example, the user has determined, or the system has learned, that the user wants to see the display after every 100 m of swimming 580. Thus, in addition to the velocity based activation of the display, the display may be activated based on the user specific display activation rule. Then, the measured quantity is distance and the measurement value is a distance value 585. A first activity type specific change in the measurement value is detected, e.g. it may be detected that the distance is greater than or equal to n*100, wherein n=1, 2, 3 . . . . This means that the first change in distance is detected every 100 m 590. In response to detecting the first activity type specific change in the measurement value, the display is activated 595, e.g. for a pre-determined time so that the user has time to see the display without actually stopping.

Figure 6:
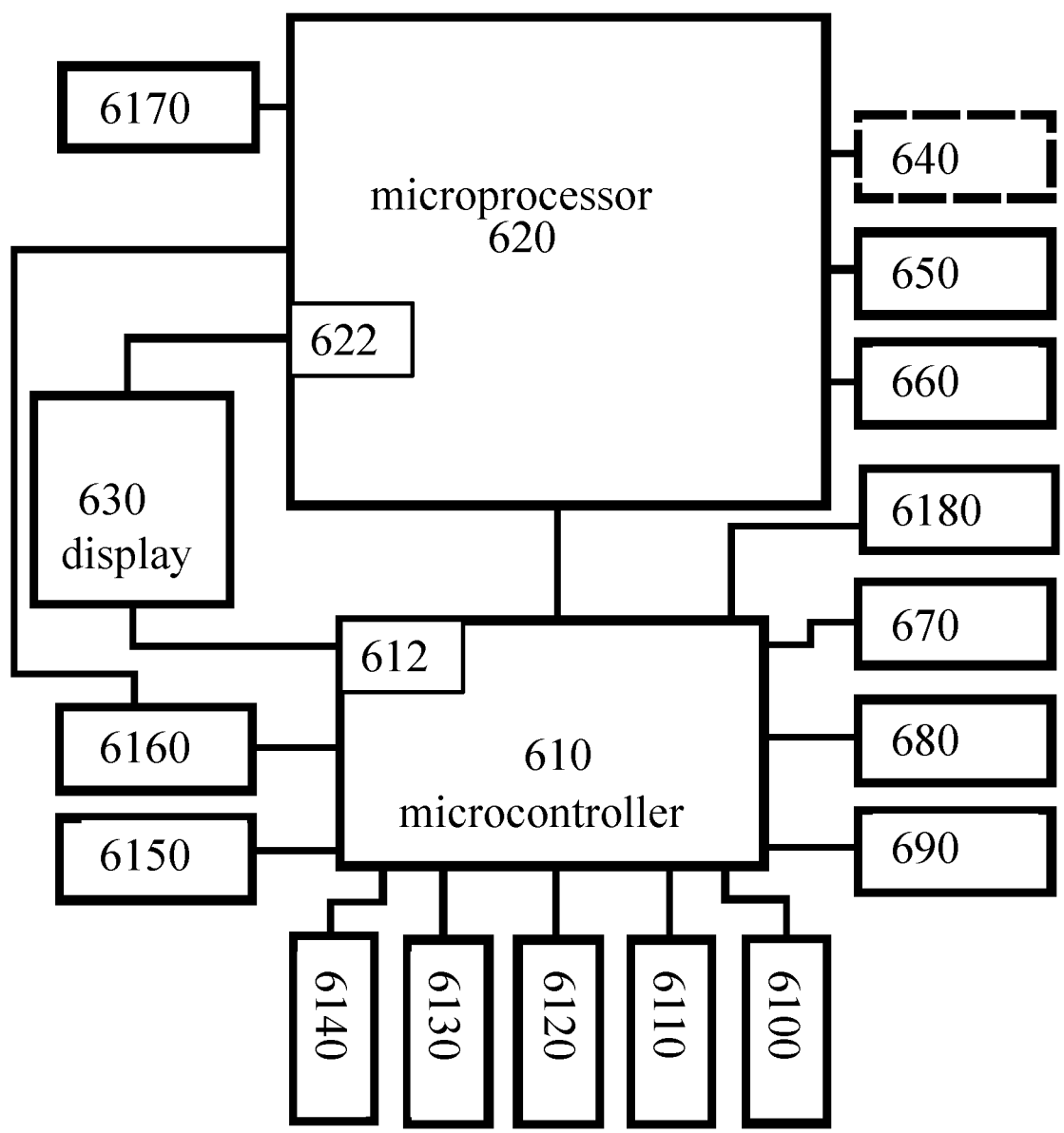
FIG. 6 shows, by way of example, a block diagram of an apparatus.

FIG. 6 shows, by way of example, a block diagram of an apparatus. The illustrated apparatus comprises a microcontroller 610 and a microprocessor 620. Microcontroller 610 may comprise, for example, a Silabs EMF32 or a Renesas RL78 microcontroller, or similar. Microprocessor 620 may comprise, for example, a Qualcomm Snapdragon processor or an ARM Cortex-based processor. Microcontroller 610 and microprocessor 620 are in the example of FIG. 6 communicatively coupled with an inter-core interface, which may comprise, for example, a serial or a parallel communication interface. More generally an interface disposed between microcontroller 610 and microprocessor 620 may be considered an inter-processing unit interface.

Microcontroller 610 is communicatively coupled, in the illustrated example, with a buzzer 670, a universal serial bus, USB, interface 680, a pressure sensor 690, an acceleration sensor 6100, a gyroscope 6110, a magnetometer 6120, satellite positioning circuitry 6130, a Bluetooth interface 6140, user interface buttons 6150 and a touch interface 6160. Pressure sensor 690 may comprise an atmospheric pressure sensor, for example.

Microprocessor 620 is communicatively coupled with an optional cellular interface 640, a non-cellular interface 650 and a USB interface 660. Microprocessor 620 is further communicatively coupled, via microprocessor display interface 622, with display 630. Microcontroller 610 is likewise communicatively coupled, via microcontroller display interface 612, with display 630. Microprocessor display interface 622 may comprise communication circuitry comprised in microprocessor 620. Microcontroller display interface 612 may comprise communication circuitry comprised in microcontroller 610.

Microcontroller 610 may be configured to determine whether triggering events occur, wherein responsive to the triggering events microcontroller 610 may be configured to cause microprocessor 620 to transition into and out of the hibernating state described above. When microprocessor 620 is in the hibernating state, microcontroller 610 may control display 630 via microcontroller display interface 622. Microcontroller 610 may thus provide, when microprocessor 620 is hibernated, for example, a reduced experience to a user via display 630.

Responsive to a triggering event, microcontroller 610 may cause microprocessor 620 to transition from the hibernated state to an active state. For example, where a user indicates, for example via buttons 6150, that he wishes to originate a cellular communication connection, microcontroller 610 may cause microprocessor 620 to transition to an active state since cellular interface 640 is controllable by microprocessor 620, but, in the example of FIG. 6, not directly usable by microcontroller 610. In some embodiments, when microprocessor 620 is hibernated, also cellular interface 640 is in a hibernated state. Cellular interface 640 may comprise an electrical interface to a cellular transceiver, for example. Cellular interface 640 may comprise control circuitry of a cellular transceiver.

In various embodiments, at least two elements illustrated in FIG. 6 may be integrated on a same integrated circuit. For example, microprocessor 620 and microcontroller 610 may be disposed as processing cores in a same integrated circuit.

Where this is the case, for example, cellular interface 640 may be a cellular interface of this integrated circuit, comprised in this integrated circuit, with cellular interface 640 being controllable by microprocessor 620 but not by microcontroller 610. In other words, individual hardware features of the integrated circuit may be controllable by one of microcontroller 610 and microprocessor 620, but not both. On the other hand, some hardware features may be controllable by either processing unit. For example, USB interface 660 and USB interface 680 may be in such an integrated embodiment one and the same USB interface of the integrated circuit, controllable by either processing core.

In FIG. 6 are further illustrated memory 6170 and memory 6180. Memory 2170 is used by microprocessor 620, and may be based on a DDR memory technology, such as for example DDR2 or DDR3, for example. Memory 6180 is used by microcontroller 610, and may be based on SRAM technology, for example.

Figure 7:
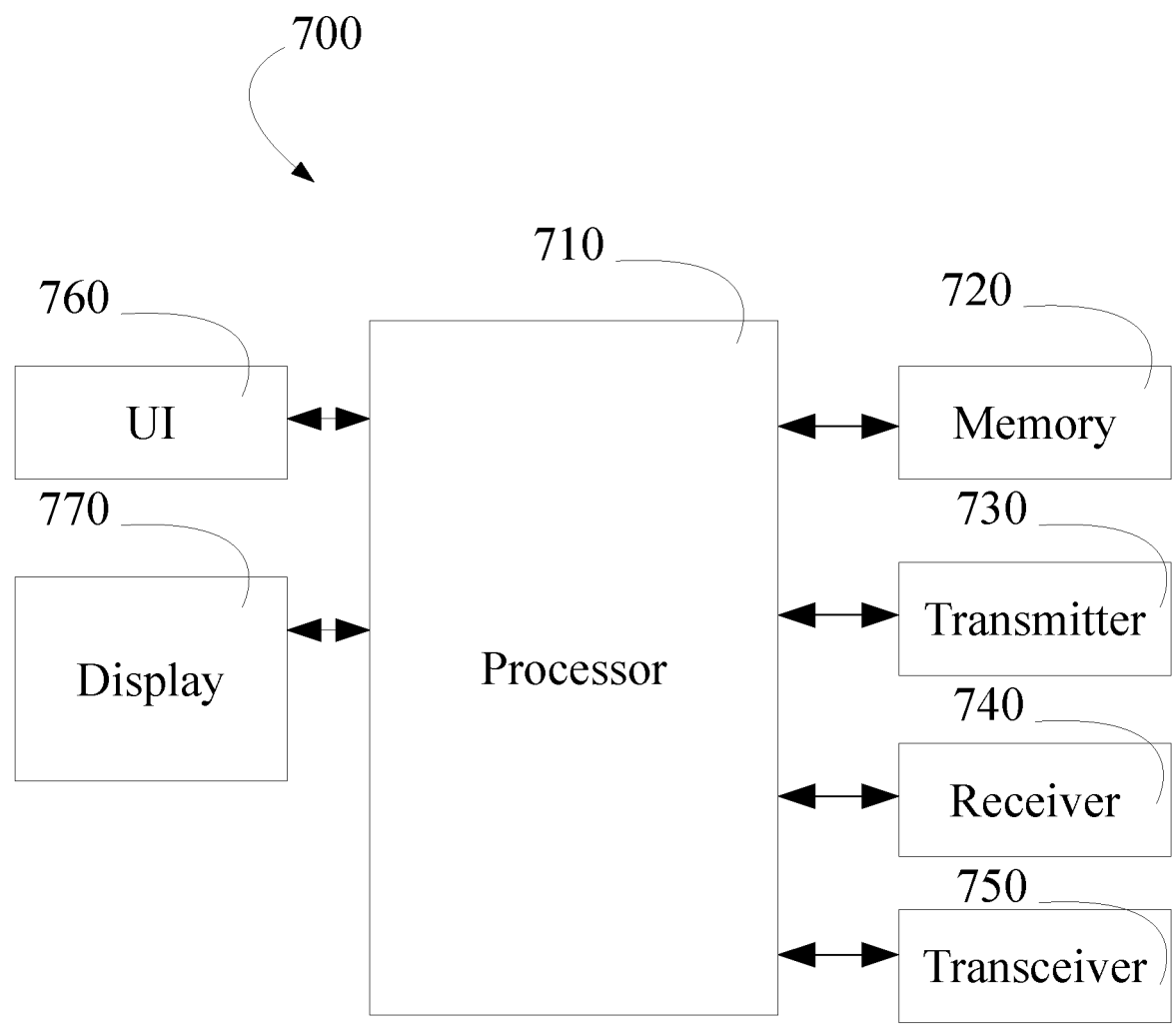
FIG. 7 shows, by way of example, a block diagram of an apparatus.

FIG. 7 shows, by way of example, a block diagram of an apparatus. Illustrated is device 700, which may comprise, for example, a wearable device such as a sport watch or smart watch 110 of FIG. 1. Comprised in device 700 is processor 710, which may comprise, for example, a single- or multi-core processor wherein a single-core processor comprises one processing core and a multi-core processor comprises more than one processing core. Processor 710 may comprise, in general, a control device. Processor 710 may comprise more than one processor, e.g. a LP processor and a HP processor, as shown in FIG. 3. Processor 710 may be a control device. A processing core may comprise, for example, a Cortex-A8 processing core manufactured by ARM Holdings or a Steamroller processing core designed by Advanced Micro Devices Corporation. Processor 710 may comprise at least one Qualcomm Snapdragon and/or Intel Atom processor. Processor 710 may comprise at least one application-specific integrated circuit, ASIC. Processor 710 may comprise at least one field-programmable gate array, FPGA. Processor 710 may be means for performing method steps in device 700. Processor 710 may be configured, at least in part by computer instructions, to perform actions.

Device 700 may comprise memory 720. Memory 720 may comprise random-access memory and/or permanent memory. Memory 720 may comprise at least one RAM chip. Memory 720 may comprise solid-state, magnetic, optical and/or holographic memory, for example. Memory 720 may be at least in part accessible to processor 710. Memory 720 may be at least in part comprised in processor 710. Memory 720 may be means for storing information. Memory 720 may comprise computer instructions that processor 710 is configured to execute. When computer instructions configured to cause processor 710 to perform certain actions are stored in memory 720, and device 700 overall is configured to run under the direction of processor 710 using computer instructions from memory 720, processor 710 and/or its at least one processing core may be considered to be configured to perform said certain actions. Memory 720 may be at least in part comprised in processor 710. Memory 720 may be at least in part external to device 700 but accessible to device 700.

Device 700 may comprise a transmitter 730. Device 700 may comprise a receiver 740. Transmitter 730 and receiver 740 may be configured to transmit and receive, respectively, information in accordance with at least one cellular or non-cellular standard. Transmitter 730 may comprise more than one transmitter. Receiver 740 may comprise more than one receiver. Transmitter 730 and/or receiver 740 may be configured to operate in accordance with global system for mobile communication, GSM, wideband code division multiple access, WCDMA, 5G, long term evolution, LTE, IS-95, wireless local area network, WLAN, Ethernet and/or worldwide interoperability for microwave access, WiMAX, standards, for example.

Device 700 may comprise a near-field communication, NFC, transceiver 750. NFC transceiver 750 may support at least one NFC technology, such as NFC, Bluetooth, Wibree or similar technologies.

Device 700 may comprise user interface, UI, 760. UI 760 may comprise at least one of a display, buttons, a keyboard, a touchscreen, a vibrator arranged to signal to a user by causing device 700 to vibrate, a speaker and a microphone. A user may be able to operate device 700 via UI 760, for example to start and/or stop an activity session, to input an activity type, to activate or deactivate a display, to manage digital files stored in memory 720 or on a cloud accessible via transmitter 730 and receiver 740, or via NFC transceiver 750.

Device 700 may comprise, or may be coupled to, a display 770. The display may be operated by the processor(s) as described in the context of FIG. 3.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the following description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

The invention claimed is:

1. An apparatus comprising at least one processor; and at least one memory including computer program code, the at least one memory and the computer program code configured to, with the at least one processor, cause the apparatus at least to perform:
    receiving an activity type of a user, wherein the activity type is selected by the user from a plurality of activity types or determined based on sensor data;
    receiving sensor data during the activity;
    determining at least one measurement value based on the sensor data;
    detecting at least one first activity type specific change in the at least one measurement value, wherein the detecting comprises detecting a change in the measurement value and comparing the detected change to an activity type specific reference value, wherein the at least one first activity type specific change is specific to the received activity type; and
    in response to detecting the at least one first activity type specific change in the at least one measurement value, activating a display by waking up one or more processors configured to control the display, from a deactivated state, wherein the one or more processors are shut down in the deactivated state,
    receiving one or more user specific display activation rules; and
    updating the activity type specific reference value according to the one or more user specific display activation rules,
and wherein the at least one activity type specific change in the at least one measurement value which causes activation of the display is pre-learned, the pre-learning comprising detecting that the display has been activated by the user a number of times in the same circumstances as defined by sensor data measured during the pre-learning, wherein the number of times is above a pre-set threshold.

2. The apparatus according to claim 1, wherein the apparatus is caused to perform:
    activating the display further based on the one or more user specific display activation rules.

3. The apparatus according to claim 1, wherein the apparatus is caused to perform:
    detecting a second activity type specific change in the measurement value, wherein the second activity type specific change is specific to the received activity type; and
    deactivating the display, from an active state, by shutting down the one or more processors configured to control the display, in response to detecting the second activity type specific change in the at least one measurement value.

4. The apparatus according to claim 1, wherein the activity type is a sport activity or sleeping.

5. The apparatus according to claim 1, wherein the sensor data comprises one or more of acceleration sensor data, gyroscope data, altimeter data, heart rate sensor data, ambient light sensor data, and position sensor data.

6. The apparatus according to claim 1, wherein the at least one measurement value is one or more of acceleration, velocity, distance, tilt, altitude, heart rate, ambient light, and location.

7. A method comprising:
    receiving an activity type of a user, wherein the activity type is selected by the user from a plurality of activity types or determined based on sensor data;
    receiving sensor data during the activity;
    determining at least one measurement value based on the sensor data;
    detecting at least one first activity type specific change in the at least one measurement value, wherein the detecting comprises detecting a change in the measurement value and comparing the detected change to an activity type specific reference value, wherein the at least one first activity type specific change is specific to the received activity type; and
    in response to detecting the at least one first activity type specific change in the at least one measurement value, activating a display by waking up one or more processors configured to control the display from a deactivated state, wherein the one or more processors are shut down in the deactivated state,
    receiving one or more user specific display activation rules,
    updating the activity type specific reference value according to the one or more user specific display activation rules, and
wherein the at least one activity type specific change in the at least one measurement value which causes activation of the display is pre-learned, the pre-learning comprising detecting that the display has been activated by the user a number of times in the same circumstances as defined by sensor data measured during the pre-learning, wherein the number of times is above a pre-set threshold.

8. The method according to claim 7, further comprising:
    activating the display further based on the one or more user specific display activation rules.

9. The method according to claim 7, further comprising:
    detecting a second activity type specific change in the measurement value, wherein the second activity type specific change is specific to the received activity type; and
    deactivating the display, from an active state, by shutting down the one or more processors configured to control the display, in response to detecting the second activity type specific change in the at least one measurement value.

10. The method according to claim 7, wherein the activity type is a sport activity or sleeping.

11. The method according to claim 7, wherein the sensor data comprises one or more of acceleration sensor data, gyroscope data, altimeter data, heart rate sensor data, ambient light sensor data, and position sensor data.

12. The method according to claim 7, wherein the at least one measurement value is one or more of acceleration, velocity, distance, tilt, altitude, heart rate, ambient light, and location.

13. A non-transitory computer readable medium comprising program instructions that, when executed by at least one processor, cause an apparatus to at least to perform:
receiving an activity type of a user, wherein the activity type is selected by the user from a plurality of activity types or determined based on sensor data;
receiving sensor data during the activity;
determining at least one measurement value based on the sensor data;
detecting at least one first activity type specific change in the at least one measurement value, wherein the detecting comprises detecting a change in the measurement value and comparing the detected change to an activity type specific reference value, wherein the at least one first activity type specific change is specific to the received activity type; and
in response to detecting the at least one first activity type specific change in the at least one measurement value, activating a display by waking up one or more processors configured to control the display from a deactivated state, wherein the one or more processors are shut down in the deactivated state,
receiving one or more user specific display activation rules,
updating the activity type specific reference value according to the one or more user specific display activation rules,
and wherein the at least one activity type specific change which causes activation of the display is pre-learned, the pre-learning comprising detecting that the display has been activated by the user a number of times in the same circumstances as defined by sensor data measured during the pre-learning, wherein the number of times is above a pre-set threshold.

* * * * *